United States Patent [19]

Broughton et al.

[11] Patent Number: 5,631,269

[45] Date of Patent: May 20, 1997

[54] DOPAMINE RECEPTOR SUBTYPE LIGANDS

[75] Inventors: Howard B. Broughton, Harlow; Ian J. Collins, Ware; Raymond Baker, Much Hadham; Paul D. Leeson, Cambridge; Michael Rowley, Harlow, all of United Kingdom

[73] Assignee: Merck Sharp & Dohme Limited, Hoddesdon, England

[21] Appl. No.: 424,364

[22] PCT Filed: Oct. 22, 1993

[86] PCT No.: PCT/GB93/02190

§ 371 Date: Apr. 20, 1995

§ 102(e) Date: Apr. 20, 1995

[87] PCT Pub. No.: WO94/10145

PCT Pub. Date: May 11, 1994

[30] Foreign Application Priority Data

Oct. 23, 1992 [GB] United Kingdom ............... 9222263
Oct. 23, 1992 [GB] United Kingdom ............... 9222265

[51] Int. Cl.$^6$ ............... A61K 31/445; C07D 211/28
[52] U.S. Cl. ............... 514/326; 514/318; 514/323; 546/194; 546/201; 546/209; 546/211
[58] Field of Search ............... 546/193, 194, 546/209, 211; 548/214, 247, 375.1; 514/318, 326, 331

[56] References Cited

U.S. PATENT DOCUMENTS 5,041,455  8/1991  Sauerberg et al. ............... 514/342
5,262,427  11/1993  Nielson et al. ............... 514/304
5,409,946  4/1995  Garvey et al. ............... 514/372

OTHER PUBLICATIONS

Ferles, M. et al, Collect. Czech. Chem. Commun. 1990, 55(5), pp. 1228–1233.

*Primary Examiner*—C. Warren Ivy
*Assistant Examiner*—Garth M. Dahlen
*Attorney, Agent, or Firm*—Mary A. Appollina; Melvin Winkokur; John Thompson

[57] ABSTRACT

Compounds of formula (I)

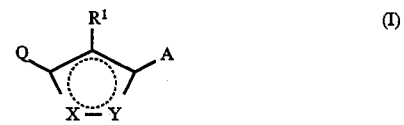

wherein one of X and Y represents nitrogen, and the other of X and Y represents oxygen, sulphur or N—$R^2$; Q represents a substituted five- or six- membered monocyclic heteroaliphatic ring which contains one nitrogen atom as the sole heteroatom and is linked to the five-membered heteroatomic ring containing the moieties X and Y via a carbon atom; as well as substituted 1,3-dioxopropane precursors thereto, are ligands for dopamine receptor subtypes within the body and are therefore useful in the treatment of disorders of the dopamine system, in particular schizophrenia.

9 Claims, No Drawings

DOPAMINE RECEPTOR SUBTYPE LIGANDS

This application is a 371 of PCT/GB 93/02190 filed Oct. 22, 1993.

This invention relates to five-membered heteroaromatic compounds, and to beta-dicarbonyl precursors thereto, which are ligands for dopamine receptor subtypes within the body. More particularly, the invention is concerned with substituted isoxazole, isothiazole and pyrazole derivatives, and with substituted 1,3-dioxopropane precursors thereto. Being ligands for dopamine receptor subtypes within the body, the compounds according to the invention are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

EP-A-0296721 and EP-A-0316718 describe inter alia substituted piperidine derivatives which are stated to be muscarinic agonists and hence potentially useful in the treatment of inter alia Alzheimer's disease.

In EP-A-0135781 and EP-A-0402644 there is described a class of indazole and related fused bicyclic heteroaromatic derivatives which are alleged to have antipsychotic activity.

The compounds in accordance with the present invention, being ligands for dopamine receptor subtypes within the body, are accordingly of use in the treatment and/or prevention of disorders of the dopamine system.

In one aspect, therefore, the present invention provides a compound of formula I, or a salt thereof or a prodrug thereof:

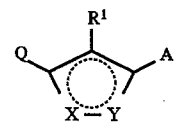

wherein the broken circle represents two non-adjacent double bonds in any position within the five-membered ring;

one of X and Y represents nitrogen, and the other of X and Y represents oxygen, sulphur or N—$R^2$;

$R^1$ represents hydrogen, halogen, $C_{1-6}$ alkyl, hydroxy or $C_{1-6}$ alkoxy;

$R^2$ represents hydrogen or $C_{1-6}$ alkyl;

A represents a group of formula (i), (ii) or (iii):

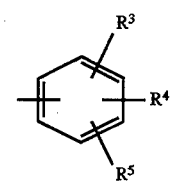

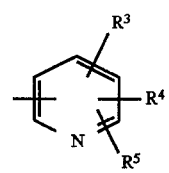

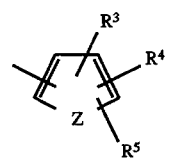

in which Z represents oxygen, sulphur or NH;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$S_2NR^aR^b$, —$NR^aR^b$, —$NR^aCOR^b$, —$NR^aCO_2R^b$, —$COR^a$, —$C_2R^a$, or —$CONR^aR^b$;

$R^a$ and $R^b$ independently represent hydrogen, hydrocarbon or a heterocyclic group; and Q represents a ring of formula Qa to Qe:

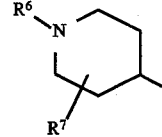

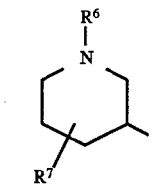

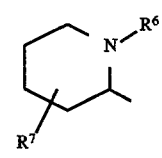

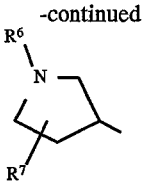

(Qd)

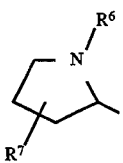

(Qe)

in which $R^6$ represents $C_{2-6}$ alkenyl, $C_{3-7}$ cycloalkyl($C_{1-6}$)alkyl, aryl, aryl($C_{1-6}$)alkyl, aryl($C_{2-6}$)alkenyl or heteroaryl ($C_{1-6}$)alkyl, any of which groups may be optionally substituted; and $R^7$ represents hydrogen, $C_{1-6}$ alkyl, $C_{2-6}$ alkenyl, $C_{3-7}$ cycloalkyl($C_{1-6}$)alkyl, aryl, aryl($C_{1-6}$)alkyl, aryl($C_{2-6}$)alkenyl or heteroaryl($C_{1-6}$)alkyl, any of which groups may be optionally substituted.

The five-membered heteroaromatic ring containing the moieties X and Y represented by formula I above may be a substituted isoxazole, isothiazole or pyrazole ring, preferably isoxazole or pyrazole.

The monocyclic heteroaliphatic ring Q in the compounds of formula I above represents a substituted pyrrolidyl or piperidyl moiety linked through carbon.

Particular monocyclic heteroaliphatic rings represented by the substituent Q in formula I include the rings of structure Qa, Qb and Qd above, especially Qa.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterooycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular $C_{3-7}$ cycloalkyl($C_{1-6}$)alkyl groups include cyclopropylmethyl and cyclohexylmethyl.

Particular aryl groups include phenyl, naphthyl and tetrahydronaphthyl.

Particular aryl($C_{1-6}$)alkyl groups include benzyl, naphthylmethyl, phenethyl and phenylpropyl.

Particular aryl($C_{2-6}$)alkenyl groups include phenylethenyl and phenylpropenyl.

A particular aryl($C_{2-6}$)alkynyl group is phenylethynyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, indolyl, imidazolyl, oxadiazolyl and thiadiazolyl groups.

Particular heteroaryl($C_{1-6}$)alkyl groups include pyridylmethyl, furylmethyl, indolylmethyl, pyrazinylmethyl and pyridylethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially chlorine.

The compounds of formula I above may be prepared by a process which comprises reacting a compound of formula II with a compound of formula III:

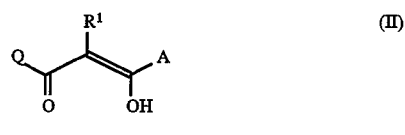

wherein Q, $R^1$ and A are as defined above, and $X^a$ represents oxygen, sulphur or $N-R^2$ in which $R^2$ is as defined above; followed, if necessary, by separation of the resulting mixture of isomers by conventional means.

The reaction is conveniently carried out by stirring the reactants in a suitable solvent, for example a mixture of N,N-dimethylformamide and methanol, optionally in the presence of a non-nucleophilic base such as ethyldiisopropylamine, suitably at room temperature. Depending upon the nature of the reactants and of the chosen reaction conditions, the reaction may afford the desired product in a single step, or may proceed via the intermediate IV:

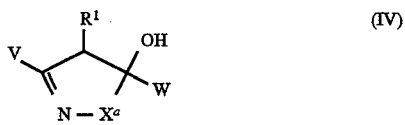

wherein one of V and W represents the group Q and the other represents the group A; and Q, A, $R^1$ and $X^a$ are as defined above.

The intermediate IV can be converted into the corresponding product of formula I by dehydration. This is conveniently effected by converting the hydroxy group into a leaving group, suitably by treatment with methanesulphonyl chloride in dichloromethane at 0° C., and treating the resulting compound, ideally in situ, with a base such as triethylamine.

As indicated above, the overall reaction between compounds II and III will usually give rise to a mixture of isomeric products of formula I, in one of which X represents nitrogen and Y represents oxygen, sulphur or N—$R^2$, and in the other of which the X and Y moieties are reversed. For this reason, it will generally be necessary to separate the mixture of isomers obtained therefrom by conventional methods such as chromatography.

The compounds of formula II above are active in their own right as ligands for dopamine receptor subtypes within the body. These compounds, and salts thereof and prodrugs thereof, accordingly represent a further aspect of the present invention.

As will be appreciated, the compounds of formula II as depicted above will generally exist in equilibrium with their other tautomeric forms, including structures (A) and (B):

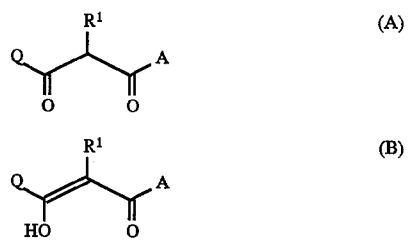

wherein Q, $R^1$ and A are as defined above. It is to be understood that all tautomeric forms of the compounds of formula II, as well as all possible mixtures thereof, are included within the scope of the present invention.

For use in medicine, the salts of the compounds of formulae I and II will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formulae I and II above. In general, such prodrugs will be functional derivatives of the compounds of formulae I and II which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituent $R^1$ represents hydrogen, halogen, $C_{1-6}$ alkyl or $C_{1-6}$ alkoxy, especially hydrogen, methyl, ethyl, methoxy or chloro.

Suitably, the substituent $R^2$ represents hydrogen or methyl, especially hydrogen.

Suitably, Z is sulphur.

Suitable values for the substituents $R^3$, $R^4$ and $R^5$ include hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, nitro, methoxy and chloro. Suitably, at least one of $R^3$, $R^4$ and $R^5$ is other than hydrogen, especially chloro.

As defined above, the substituents $R^6$ and $R^7$ may represent $C_{2-6}$ alkenyl, $C_{3-7}$ cycloalkyl($C_{1-6}$)alkyl aryl, aryl($C_{1-6}$)alkyl, aryl($C_{2-6}$)alkenyl or heteroaryl($C_{1-6}$)alkyl, any of which groups may be optionally substituted. In addition, $R^7$ may represent hydrogen or optionally substituted $C_{1-6}$ alkyl. Examples of suitable substituents on the groups $R^6$ and/or $R^7$ include $C_{1-6}$ alkyl, halogen, $C_{1-6}$ alkoxy, keto and nitro.

Particular values of $R^6$ and $R^7$ include allyl, cyclopropylmethyl, cyclohexylmethyl, tetrahydronaphthyl, benzyl, methyl-benzyl, chlorobenzyl, dichlorobenzyl, methoxy-benzyl, nitro-benzyl, naphthylmethyl, phenethyl, methoxy-phenethyl, phenylcarbonylmethyl, phenylpropyl, phenyl-propenyl, furylmethyl, indolylmethyl and pyridylethyl. In addition, $R^7$ may suitably represent hydrogen or methyl. Preferably, $R^7$ represents hydrogen.

A particular sub-class of compounds according to the invention is represented by the compounds of formula IA, and salts and prodrugs thereof:

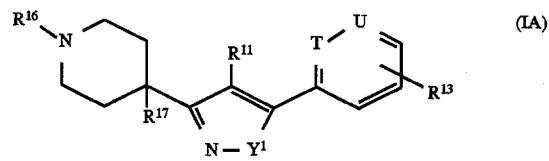

wherein $Y^1$ represents oxygen, sulphur or N—$R^{12}$;

one of T and U represents CH and the other represents CH or N, preferably CH;

$R^{11}$ represents hydrogen, halogen, $C_{1-6}$ alkyl or $C_{1-6}$ alkoxy;

$R^{12}$ represents hydrogen or $C_{1-6}$ alkyl;

$R^{13}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl;

$R^{16}$ represents $C_{2-6}$ alkenyl, $C_{3-7}$ cycloalkyl($C_{1-6}$)alkyl, aryl, aryl($C_{1-6}$)alkyl, aryl($C_{2-6}$)alkenyl or heteroaryl ($C_{1-6}$)alkyl, any of which groups may be optionally substituted; and $R^{17}$ represents hydrogen or methyl, preferably hydrogen.

Examples of suitable substituents on the group $R^{16}$ include one or more of $C_{1-6}$ alkyl, halogen, $C_{1-6}$ alkoxy, keto and nitro.

Particular values of $R^{16}$ with reference to formula IA above include allyl, cyclopropylmethyl, cyclohexylmethyl, tetrahydronaphthyl, benzyl, methyl-benzyl, chlorobenzyl, dichlorobenzyl, methoxy-benzyl, nitro-benzyl, naphthylmethyl, phenethyl, methoxy-phenethyl, phenylcarbonylmethyl, phenylpropyl, phenyl-propenyl, furylmethyl, indolylmethyl and pyridylethyl.

Particular values of $Y^1$ with reference to formula IA above include oxygen or N—$R^{12}$, preferably oxygen, NH or N-methyl.

Particular values of $R^{11}$ include hydrogen, methyl, ethyl, methoxy and chloro.

Suitably, $R^{12}$ represents hydrogen or methyl, especially hydrogen.

Particular values of $R^{13}$ include hydrogen, methyl, ethyl, isopropyl, nitro, methoxy and chloro, especially chloro.

Another sub-class of compounds according to the invention is represented by the compounds of formula IB, and salts and prodrugs thereof:

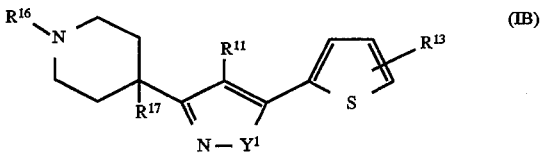

wherein $Y^1$, $R^{11}$, $R^{13}$, $R^{16}$ and $R^{17}$ are as defined with reference to formula IA above.

A further sub-class of compounds according to the invention is represented by the compounds of formula IC, and salts and prodrugs thereof:

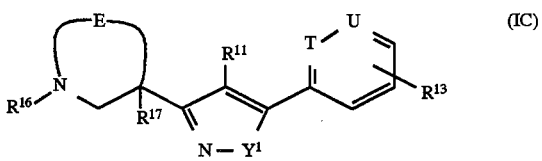

wherein

E represents a linking group of formula —(CH$_2$)$_2$— or —(CH$_2$)$_3$—; and $Y^1$, T, U, $R^{11}$, $R^{13}$, $R^{16}$ and $R^{17}$ are as defined with reference to formula IA above.

A still further sub-class of compounds according to the invention is represented by the compounds of formula IIA, and salts and prodrugs thereof:

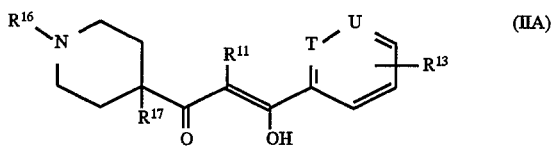

wherein

T, U, $R^{11}$, $R^{13}$, $R^{16}$ and $R^{17}$ are as defined with reference to formula IA above.

A yet further sub-class of compounds according to the invention is represented by the compounds of formula IIB, and salts and prodrugs thereof:

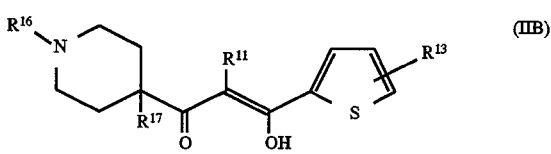

wherein $R^{11}$, $R^{13}$, $R^{16}$ and $R^{17}$ are as defined with reference to formula IA above.

An additional sub-class of compounds according to the invention is represented by the compounds of formula IIC, and salts and prodrugs thereof:

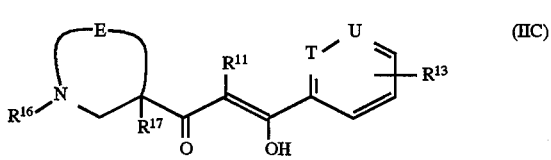

wherein

T, U, $R^{11}$, $R^{13}$, $R^{16}$ and $R^{17}$ are as defined with reference to formula IA above; and E is as defined with reference to formula IC above.

Specific compounds within the scope of the present invention include:

1-(4-chlorobenzyl)-4-[3-(4-chlorophenyl)-3-hydroxy-1-oxoprop-2-en-1-yl]piperidine;
1-benzyl-4-[3-(4-chlorophenyl)-3-hydroxy-1-oxoprop-2-en-1-yl]piperidine;
1-(4-chlorobenzyl)-4-[3-hydroxy-3-(4-nitrophenyl)-1-oxoprop-2-en-1-yl]piperidine;
4-[3-(4-chlorophenyl)-3-hydroxy-1-oxoprop-2-en-1-yl]-1-(2-phenylethyl)piperidine;
1-benzyl-3-[3-(4-chlorophenyl)-3-hydroxy-1-oxoprop-2-en-1-yl]piperidine;
4-[3-(4-chlorophenyl)-2-methyl-1,3-dioxoprop-1-yl]-1-(2-phenylethyl)piperidine;
1-benzyl-4-[3-hydroxy-1-oxo-3-(2-thienyl)prop-2-en-1-yl]piperidine;
4-[3-hydroxy-1-oxo-3-(3-pyridyl)prop-2-en-1-yl]-1-(2-phenylethyl)piperidine;
3-[1-(4-chlorobenzyl)piperidin-4-yl]-5-(4-chlorophenyl) pyrazole;
3-(1-benzylpiperidin-4-yl)-5-(4-chlorophenyl)pyrazole;
5-(4-chlorophenyl)-3-[1-(4-methylbenzyl)piperidin-4-yl]-pyrazole;
5-(4-chlorophenyl)-3-[1-(4-methoxybenzyl)piperidin-4-yl]-pyrazole;
5-(4-chlorophenyl)-3-[1-(prop-2-en-1-yl)piperidin-4-yl]-pyrazole;
5-(4-chlorophenyl)-3-[1-(4-nitrobenzyl)piperidin-4-yl]-pyrazole;
3-[1-(4-chlorobenzyl)piperidin-4-yl]-5-phenylpyrazole;
3-[1-(4-chlorobenzyl)piperidin-4-yl]-5-(2-thienyl)pyrazole;
3-[1-(4-chlorobenzyl)piperidin-4-yl]-5-(4-isopropylphenyl) pyrazole;
3-[1-(4-chlorobenzyl)piperidin-4-yl]-5-(4-methoxyphenyl) pyrazole;
5-(4-chlorophenyl)-3-(1-cyclohexylmethylpiperidin-4-yl) pyrazole;
5-(4-chlorophenyl)-3-[1-(2-phenylethyl)piperidin-4-yl]-pyrazole;
5-(4-chlorophenyl)-3-[1-(3,4-dichlorobenzyl)piperidin-4-yl]pyrazole;
3-[1-(4-chlorobenzyl)piperidin-4-yl]-5-(3-chlorophenyl) pyrazole;
3-[1-(3-chlorobenzyl)piperidin-4-yl]-5-(4-chlorophenyl) pyrazole;
5-[1-(4-chlorobenzyl)piperidin-4-yl]-3-(4-chlorophenyl)-1-methylpyrazole;
3-[1-(4-chlorobenzyl)piperidin-4-yl]-5-(4-chlorophenyl)-1-methylpyrazole;
3-[1-(4-chlorobenzyl)piperidin-4-yl]-5-(2-chlorophenyl) pyrazole;
3-(1-benzylpiperidin-4-yl)-5-phenylpyrazole;
3-[1-(4-chlorobenzyl)piperidin-4-yl]-5-(4-chlorophenyl) isoxazole;
5-[1-(4-chlorobenzyl)piperidin-4-yl]-3-(4-chlorophenyl) isoxazole;
3-[1-(4-chlorobenzyl)piperidin-4-yl]-5-(2-methoxyphenyl) pyrazole;
5-(4-chlorophenyl)-3-[1-(2-methylbenzyl)piperidin-4-yl]-pyrazole;
5-(4-chlorophenyl)-3-[1-(3-nitrobenzyl)piperidin-4-yl]-pyrazole;
5-(4-chlorophenyl)-3-[1-(3-methylbenzyl)piperidin-4-yl]-pyrazole;
5-(4-chlorophenyl)-3-[1-(2-nitrobenzyl)piperidin-4-yl]-pyrazole;
3-[1-(4-chlorobenzyl)piperidin-4-yl]-4-methyl-5-phenylpyrazole;

3-[1-(2-chlorobenzyl)piperidin-4-yl]-5-(4-chlorophenyl) pyrazole;
5-(4-chlorophenyl)-3-(1-cyclopropylmethylpiperidin-4-yl) pyrazole;
3-(1-benzylpiperidin-4-yl)-5-(4-chlorophenyl)-4-methylpyrazole;
5-(4-chlorophenyl)-3-[1-(2-naphthylmethyl)piperidin-4-yl] pyrazole;
5-(4-chlorophenyl)-3-[1-(3-phenylpropyl)piperidin-4-yl] pyrazole;
5-(4-chlorophenyl)-3-[1-(3-methoxybenzyl)piperidin-4-yl] pyrazole;
3-[1-(2-phenylethyl)piperidin-4-yl]-5-(2-pyridyl)pyrazole;
3-(1-benzyl-4-methylpiperidin-4-yl)-5-(4-chlorophenyl) pyrazole;
5-(4-chlorophenyl)-3-[1-(indol-3-ylmethyl)piperidin-4-yl] pyrazole;
5-(4-chlorophenyl)-4-methyl-3-[1-(2-phenylethyl) piperidin-4-yl]pyrazole;
3-(1-benzylpiperidin-3-yl)-5-(4-chlorophenyl)pyrazole;
3-(1-benzylpyrrolidin-3-yl)-5-(4-chlorophenyl)pyrazole;
3-(1-benzylpiperidin-4-yl)-5-(2-thienyl)isoxazole;
5-(1-benzylpiperidin-4-yl)-3-(2-thienyl)isoxazole;
5-(4-chlorophenyl)-3-[1-(2-phenylethyl)piperidin-4-yl] isoxazole;
3-(1-benzylpiperidin-4-yl)-5-(4-chlorophenyl)isoxazole;
3-(4-chlorophenyl)-4-methyl-5-[1-(2-phenylethyl) piperidin-4-yl]isoxazole;
5-(4-chlorophenyl)-4-methyl-3-[1-(2-phenylethyl) piperidin-4-yl]isoxazole;
3-(1-benzylpiperidin-4-yl)-5-(4-chlorophenyl)-4-ethylpyrazole;
5-(1-benzylpiperidin-4-yl)-3-(4-chlorophenyl)-1,4-dimethylpyrazole;
3-(1-benzylpiperidin-4-yl)-5-(4-chlorophenyl)-1,4-dimethylpyrazole;
4-methoxy-5-phenyl-3-[1-(2-phenylethyl)piperidin-4-yl] pyrazole;
5-(4-chlorophenyl)-3-[1-(3-E-phenylprop-2-en-1-yl) piperidin-4-yl]pyrazole;
5-(4-chlorophenyl)-3-[1-(1-naphthylmethyl)piperidin-4-yl] pyrazole;
3-[1-(2-furylmethyl)piperidin-4-yl]-4-methyl-5-phenylpyrazole;
3-[1-(2-(4-methoxyphenyl)ethyl)piperidin-4-yl]-4-methyl-5-phenylpyrazole;
4-methyl-3-[1-(2-oxo-2-phenylethyl)piperidin-4-yl]-5-phenylpyrazole;
4-methyl-5-phenyl-3-[1-(2-(3-pyridyl)ethyl)piperidin-4-yl] pyrazole;
5-(4-chlorophenyl)-3-[1-(1,2,3,4-tetrahydronaphth-2-yl) piperidin-4-yl]pyrazole;
4-chloro-5-(4-chlorophenyl)-3-[1-(2-phenylethyl)piperidin-4-yl]pyrazole; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosolor liquid sprays, drops, ampoules, auto-injector devices or suppositories; for oral, parenteral, intranasal, sublingualor rectal administration, or for administration by inhalation or insulfation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetylalcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula II as defined above may be prepared by reacting a carboxylic acid of formula V, or an activated derivative thereof, with two equivalents of a metal enolate of formula VI:

 (V)

 (VI)

wherein $R^1$ and A are as defined above, $Q^1$ corresponds to the moiety Q as defined above or represents a precursor thereto protected on the nitrogen atom, and M represents a metal capable of providing a suitable counterion for the enolate anion; followed, where required, by removal of the N-protecting group from the moiety $Q^1$; with subsequent attachment to the nitrogen atom thereby deprotected of an appropriate substituent by standard means to afford a product containing the desired moiety Q.

For example, the substituent $Q^1$ in compound V may represent a moiety of formula Qa to Qe as defined above, in which $R^7$ is hydrogen and $R^6$ represents an N-protecting group. Once the reaction between compounds V and VI is complete, the N-protecting group must be removed, and the desired group $R^6$ subsequently attached, by conventional methods.

The metal M is suitably an alkali metal, especially lithium.

The activated derivative of the carboxylic acid V is suitably the compound formed by reaction between the carboxylic acid V and 1,1'-carbonyldiimidazole, conveniently in tetrahydrofuran at room temperature.

Where the substituent $Q^1$ represents a precursor to the moiety Q protected on the nitrogen atom, the N-protecting group is suitably an alkoxycarbonyl moiety such as t-butoxycarbonyl(BOC), in which case the N-protecting group can conveniently be removed subsequently as necessary by treatment under acidic conditions, e.g. stirring in hydrochloric acid or trifluoroacetic acid.

The reaction between compound V, or the activated derivative thereof, and compound VI is suitably carried out in a solvent such as tetrahydrofuran, commencing at –78° C. with warming to 0° C.

The metal enolate of formula VI is ideally prepared by reacting the corresponding carbonyl compound of formula VII:

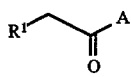
(VII)

wherein $R^1$ and A are as defined above; with a nonnucleophilic base such as lithium diisopropylamide, suitably in tetrahydrofuran at –78° C.

In an alternative process, the compounds of formula I above wherein X represents nitrogen, Y is N—$R^2$, $R^1$ is hydrogen and Q represents a group of formula Qa as defined above may be prepared by reacting a compound of formula VIII:

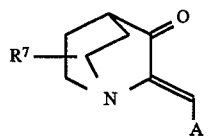
(VIII)

wherein A and $R^7$ are as defined above; with hydrazine hydrate; followed by attachment of the groups $R^6$ and $R^2$, where the latter is required to be other than hydrogen, by standard carbon-nitrogen bond-forming reactions.

The reaction of compound VIII with hydrazine hydrate is advantageously effected in the presence of ethylene glycol and a strong base such as potassium hydroxide, suitably commencing at 110° C. with warming to the reflux temperature of the reaction mixture.

The method whereby the groups $R^6$ and, where necessary, $R^2$ are attached to the product obtained from any of the above-described processes will suitably comprise a standard carbon-nitrogen bond-forming reaction known from the art, such as N-alkylation. By way of example, a compound wherein $R^6$ is hydrogen initially obtained may conveniently be N-benzylated by treatment with a benzylhalide, e.g. benzylbromide, typically under basic conditions, e.g. using triethyl amine in a mixture of dichloromethane and N,N-dimethylformamide, suitably at room temperature, to afford a product wherein $R^6$ is benzyl.

The intermediates of formula VIII above may be prepared by condensing an aldehyde of formula A—CHO with a suitable quinuclidin-3-one derivative of formula IX:

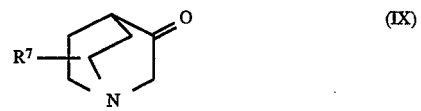
(IX)

wherein A and $R^7$ are as defined above. The reaction is conveniently carried out in a solvent such as ethanol, advantageously in the presence of a strong base such as sodium hydroxide, suitably by heating the reaction mixture at reflux.

Where they are not commercially available, the starting materials of formula III, V, VII, IX and A—CHO may be prepared by standard methods well known from the art.

It will be appreciated that any compound of formula I or formula II initially obtained from any of the above processes may, where appropriate, subsequently be elaborated into a further desired compound of formula I or formula II using techniques known from the art. For example, as alluded to above, a compound of formula I wherein $R^2$ is hydrogen initially obtained may be converted into a compound of formula I wherein $R^2$ is other than hydrogen by means of conventional N-alkylation methodology.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$_3$H]-spiperone from the human dopamine $D_4$ receptor subtype of below 1.5 µM.

In the accompanying Examples, the compounds may exist in the solvent in which the NMR spectrum is recorded as a mixture of ketone and enoltautomers. The NMR spectrum is quoted for the major form, and small peaks corresponding to other tautomers are not recorded.

EXAMPLE 1

1-(4-Chlorobenzyl)-4-(3-hydroxy-1-oxo-3-(4-chlorophenyl)prop-2-en-1-yl)piperidine n-Butyllithium (28 ml, 1.6M in hexanes) was added to diisopropylamine (6.2 ml) in tetrahydrofuran (150 ml) at 0° C. The solution was stirred at 0° C. for 15 min then cooled to −78° C., and a solution of 4-chloroacetophenone (6.8 g) in THF (10 ml) added over 5 min. In a separate vessel, carbonyldiimidazole (3.89 g) was added to 1-tert-butyloxycarbonyl-4-piperidine carboxylic acid (5 g) in THF (100 ml). After 45 min, the latter solution was cannulated into the former, stirred for 45 min at −78° C. then warmed to room temperature. Ethyl acetate was added and the mixture washed with 1M citric acid, saturated sodium hydrogen carbonate solution, and brine, dried (MgSO$_4$), and evaporated in vacuo. A saturated solution of HCl in ethyl acetate (50 ml) was added to the resulting oil and the mixture stirred at room temperature for 30 min then stood at 0° C. for 1 h. The resulting solid was collected, washed with ethyl acetate and dried, to give 4-(1-(3-hydroxy-1-oxo-3-(4-chlorophenyl)-2-propenyl))piperidine hydrochloride as an off-white solid (5.1 g). 3 g of this solid was suspended in dimethylformamide (30 ml) and dichloromethane (30 ml), then triethylamine (3.1 ml) and 4-chlorobenzyl chloride (1.77 g) added. After stirring for 70 h the mixture was evaporated, diluted with ethyl acetate, washed with water and brine, dried, and evaporated in vacuo to give 1-(4-chlorobenzyl)-4-(1-(3-hydroxy-1-oxo-3-(4-chlorophenyl)-2-propenyl))piperidine (2.3 g) as cubes, mp 91°–92° C. (from ethyl acetate/hexanes) (Found: C, 64.40; H, 5.68; N, 3.61. $C_{21}H_{21}NO_2Cl$ requires C, 64.62; H, 5.42; N, 3.59%); $\delta_H$ (360 MHz, CDCl$_3$) 1.8–2.0 (4H, m, C$\underline{H}_2$CH), 2.0–2.1 (2H, m, NC$\underline{H}_A$H$_B$CH$_2$), 2.3–2.4 (1H, m, C$\underline{H}$CH$_2$), 2.96 (2H, d, J=12, NCH$_A$H$_B$CH$_2$), 3.5 (2H, s, ArC$\underline{H}_2$), 6.14 (1H, s, C=CH), 7.29 (4H, s, ArHCH$_2$), 7.41 (2H, d, J=8.6, ArHo to Cl), 7.81 (2H, d, J=8.6, ArHm to Cl), 15.9 (1H, brs, OH); m/z (CI$^+$, NH$_3$), 390 ($\underline{M}^+$+H).

EXAMPLE 2

1-Benzyl-4-(3-hydroxy-1-oxo-3-(4-chlorophenyl)-2-prop-2-en-1-yl)piperidine

White needles, mp 84°–86° C. (from ethanol/water) (Found: C, 71.21; H, 6.29; N, 3.91. $C_{21}H_{22}NO_2Cl$ requires C, 70.88; H, 6.23; N, 3.94%); $\delta_H$ (360 MHz, CDCl$_3$) 1.8–2.0 (4H, m, C$\underline{H}_2$CH), 2.0–2.2 (2H, m, NC$\underline{H}_A$H$_B$CH$_2$), 2.3–2.4 (1H, m, C$\underline{H}$CH$_2$), 3.0 (2H, d, J=12, NCH$_A$H$_B$CH$_2$), 3.59 (2H, s, ArC$\underline{H}_2$), 6.15 (1H, s, C=CH), 7.2–7.4 (5H, m, Ph), 7.42 (2H, d, J=8.6, ArHo to Cl), 7.81 (2H, d, J=8.6, ArHm to Cl), 15.9 (1H, brs, OH); m/z (CI$^+$, NH$_3$) 356 ($\underline{M}^+$+H).

EXAMPLE 3

1-(4-Chlorobenzyl)-4-(3-hydroxy-1-oxo-3-(4-nitrophenyl)prop-2-en-1-yl)piperidine, hydrogen oxalate salt mp 225°–230° C. (from ethanol) (Found: C, 56.82; H, 5.15; N, 6.17. $C_{21}H_{21}N_2O_4Cl+0.95C_2H_2O_4$ requires C, 56.92; H, 4.78; N, 5.80%); $\delta_H$ (360 MHz, d$_6$-DMSO) 1.8–2.0 (2H, m, C$\underline{H}_A$H$_B$CH), 2.05 (2H, d, J=13, CH$_A$H$_B$CH), 2.7–2.8 (3H, m, NC$\underline{H}_A$H$_B$CH$_2$ and CH$_2$CH), 3.2–3.3 (2H, m, NCH$_A$H$_B$CH$_2$), 4.10 (2H, s, ArCH$_2$), 6.78 (1H, s, C=CH), 7.5–7.8 (4H, m, ArHCH$_2$), 8.20 (2H, d, J=8.9, ArHNO$_2$), 8.36 (2H, d, J=8.9, ArHNO$_2$); m/z (CI$^+$, NH$_3$) 401 (M$^+$+H).

EXAMPLE 4

1-(2-Phenylethyl)-4-(3-hydroxy-1-oxo-3-(4-chlorophenyl)-prop-2-en-1-yl)piperidine, hydrogen oxalate salt White powder, mp 180°–182° C. (from ethanol) (Found: C, 61.95; H, 5.76; N, 3.01. $C_{22}H_{24}NO_2Cl+C_2H_2O_4+0.3H_2O$ requires C, 62.00; H, 5.76; N, 3.08%); $\delta_H$ (360 MHz, d$_6$-DMSO) 1.9–2.0 (2H, m, C$\underline{H}_A$H$_B$CH), 2.09 (2H, d, J=12.5, CH$_A$H$_B$CH), 2.6–2.7 (1H, m, CH$_2$CH), 2.8–3.0 (4H, m, ArCH$_2$ and NC$\underline{H}_A$H$_B$CH$_2$CH), 3.1–3.2 (2H, m, ArCH$_2$CH$_2$N), 3.48 (2H, d, J=11.8, NCH$_A$H$_B$CH$_2$CH), 6.65 (1H, s, C=CH), 7.2–7.4 (5H, m, Ph), 7.60 (2H, d, J=8.6, ArHo to Cl), 7.99 (2H, d, J=8.6, ArHm to Cl); m/z (CI$^+$, NH$_3$) 370 ($\underline{M}^+$+H).

EXAMPLE 5

1-Benzyl-3-(3-hydroxy-1-oxo-3-(4-chlorophenyl) prop-2-en-1-yl)piperidine hydrobromide White needles, mp 193°–194° C. (from EtOH); (Found: C, 57.63; H, 5.33; N, 3.31. $C_{21}H_{23}NO_2ClBr$ requires C, 57.75; H, 5.31; N, 3.21%); $\delta_H$ (360 MHz, d$_6$-DMSO+ CF$_3$CO$_2$H) 1.42 (1H, apparent qd, J=12 and 3, 1 of NCH$_2$C$\underline{H}_2$CH$_2$), 1.64–2.20 (3H, m, 3 of NCH$_2$C$\underline{H}_2$C$\underline{H}_2$), 2.90–3.18 (2H, m, 2 of NCH$_2$), 3.32–3.60 (3H, m, 2 of NCH$_2$ and NCH$_2$CH), 4.38 (2H, br s, NCH$_2$Ar), 6.68 (1H, s, C=CH), 7.45–7.70 (7H, m, Ph and ArHo to Cl) and 8.05 (2H, d, J=9, ArHm to Cl); (CI$^+$, NH$_3$) 356 ($\underline{M}^+$+H; 70%), 322 (20), 266 (18), 218 (80), 174 (30), 128 (50); 106 (80) and 84 (100); m/z (CI$^-$, NH$_3$) 355 ($\underline{M}^-$; 40%), 265 (15), 127 (30) and 81 (100).

EXAMPLE 6

1-(2-Phenylethyl)-4-(1,3-dioxo-2-methyl-3-(4-chlorophenyl)prop-1-yl)piperidine hydrochloride White granules, mp 179°–181° C. (from EtOH-EtOAc); (Found: C, 65.50; H, 6.56; N, 3.38. $C_{23}H_{27}NO_2Cl_2$ requires C, 65.71; H, 6.47; N, 3.33%); $\delta_H$ (360 MHz, CDCl$_3$) ca. 1:1 mixture of isomers of the protonated piperidine, 1.40 (3H, d, J=7, CH$_3$ both isomers), 1.95–2.13 (4H+2H, m, NCH$_2$CH$_A$H$_B$ both isomers and NCH$_2$CH$_A$H$_B$ one isomer), 2.40–2.59 (2H+2H, m, NCH$_2$CH$_A$H$_B$ other isomer and NC$\underline{H}_A$H$_B$ one isomer), 2.72–2.82 (2H, m, NC$\underline{H}_A$H$_B$ other isomer), 3.02–3.30 (5H+5H, NCH$_2$CH$_2$Ar, NCH$_2$C$\underline{H}_2$Ar, and N(CH$_2$)$_2$C$\underline{H}$ both isomers), 3.40 (2H, apparent t, J=12, NCH$_A$H$_B$ one isomer), 3.64 (2H, apparent dd, J=14 and 12, NCH$_A$H$_B$ other isomer), 4.69 (1H+1H, q, J=7, C$\underline{H}$CH$_3$ both isomers), 7.22–7.40 (5H+5H, m, Ph both isomers), 7.49 (2H, d, J 8, ArH$_o\ to\ Cl$ one isomer), 7.50 (2H, d, J=8, ArHo to Cl other isomer), 7.91 (2H, d, J=8, ArHm to Cl one isomer), 7.93 (2H, d, J=8, ArHm to Cl other isomer), 12.39 (1H, br s, $^+$NH one isomer) and 12.51 (1H, br s, $^+$NH other isomer); m/z (CI$^+$, NH$_3$) 384 ($\underline{M}^+$+H; 100%); m/z (CI$^-$, NH$_3$) 419 ( $\underline{M}^-$+Cl; 10%) and 383 (M$^-$-H; 100).

EXAMPLE 7

1-Benzyl-4-(3-hydroxy-1-oxo-3-(2-thienyl)prop-2-en-1-yl)piperidine

Yellow crystals, mp 80°–83° C. (from ethanol/water). (Found: C, 69.48; H, 6.21; N, 3.93. C$_{19}$H$_{21}$NO$_2$S requires C, 69.69; H, 6.46; N, 4.28%); δ$_H$ (360 MHz, d$_6$-DMSO), 1.63 (2H, dq, J=3.5 and 9.0 Hz, CH$_A$H$_B$CH), 1.81 (2H, br d, J=11 Hz, CH$_A$H$_B$CH), 1.93–2.01 (2H, m, CH$_A$H$_B$N), 2.2–2.3 (1H, m, CH$_2$CHCH$_2$), 2.87 (2H, br d, J=11.7 Hz, CH$_A$H$_B$N), 3.48 (2H, s, ArCH$_2$), 6.43 (1H, s, CCH, 7.23–7.35 (6H, m, Ar H), 7.92–8.04 (2H, m, ArH); m/z (CI$^+$, NH$_3$) 328 ( $\underline{M}^+$+H).

EXAMPLE 8

1-(2-Phenylethyl)-4-(3-hydroxy-1-oxo-3-(3-pyridyl)prop-2-en-1-yl)piperidine

Tan needles, mp 75°–77° C. (from ethanol/water) (Found: C, 73.93; H, 7.20; N, 8.02. C$_{21}$H$_{24}$N$_2$O$_2$+0.25H$_2$O requires C, 73.98; H, 7.24; N, 8.22%); δ$_H$ (360 MHz, CDCl$_3$)1.8–2.0 (4H, m, CH$_2$'s), 2.1–2.2 (2H, m, CH$_2$), 2.37–2.42 (1H, m, CHCO), 2.6–2.7 (2H, m, CH$_2$), 2.8–2.9 (2H, m, CH$_2$), 3.1–3.2 (2H, m, CH$_2$), 6.22 (1H, s, C=CH), 7.1–7.3 (5H, m, Ph), 7.40 (1H, dd, J=6 and 8 Hz, pyridine H-5), 8.18 (1H, dt, J=8 and 2 Hz, pyridine H-4), 8.72 (1H, dd, J=6 and 2 Hz, pyridine H-6), 9.08 (1H, d, J=2 Hz, pyridine H-2), 16.0 (1H, br s, OH); m/z (CI$^+$, NH$_3$) 337 ($\underline{M}^+$+H).

EXAMPLE 9

3-(1-(4-Chlorobenzyl)-4-piperidinyl)-5-(4-chlorophenyl)pyrazole a) 2-(4-Chlorobenzylidene)quinuclidin-3-one

A solution of 3-quinuclidinone (54.5 g), 4-chlorobenzaldehyde (84.0 g) and sodium hydroxide (3.50 g) in absolute ethanol (400 cm$^3$) was heated at reflux for 2.5 hours. The mixture was cooled and addition of water (100 cm$^3$) caused the product to precipitate as an orange solid. The precipitate was collected and washed with 1:1 ethanol-water (400 cm$^3$). The mother-liquors were stood for 2 days, after which time further precipitated material was collected. The orange solid was redissolved in dichloromethane (800 cm$^3$) and washed with water (200 cm$^3$). The organic phase was dried (MgSO$_4$), filtered and evaporated to dryness to give the title compound as a bright yellow powder (86.2 g, 76%), mp. 108°–110° C.; δ$_H$ (360 MHz; CDCl$_3$) 1.99–2.05 (4H, m, 2×NCH$_2$CH$_2$), 2.63 [(1H, quintet, J=2.9, (CH$_2$)$_2$CH], 2.92–3.01 (2H, m, 2×NCH), 3.11–3.19 (2H, m, 2×NCH), 6.95 (1H, s, C=CH), 7.33 (2H, d, J=8.6, 2×ArH o to Cl) and 7.98 (2H, d, J=8.6, 2×ArH m to Cl); m/z (CI$^+$; NH$_3$) 248 (M$^+$+H, 100%).

b) 3-(4-Piperidinyl)-5-(4-chlorophenyl)pyrazole

A mixture of 2-(4-chlorobenzylidene)quinuclidin-3-one (35.0 g), potassium hydroxide (15.0 g) and hydrazine hydrate (11.0 cm$^3$) in ethylene glycol(100 cm$^3$) was heated at 110° C. for 15 minutes to produce a clear, dark brown solution. Hydrazine hydrate and water were distilled from the solution over 1 hour at 110° C. to 195° C. The brown solution was then heated at reflux for 3 hours. The mixture was cooled to room temperature and diluted with water (300 cm$^3$). The resulting white precipitate was collected and washed with water (500 cm$^3$) and ethyl acetate (200 cm$^3$). The white powder was dried in vacuo to give the title compound (31.5 g, 85%), m.p. 174°–176° C.; δ$_H$ (250 MHz; d$_6$-DMSO) 1.52 (2H, apparent qd, J=12 and 4, 2×NCH$_2$CH$_A$H$_B$), 1.85 (2H, apparent d, J=10, 2×NCH$_2$CH$_A$H$_B$), 2.56 (2H, apparent td, J=12 and 2, 2×NCH$_A$H$_B$), 2.71 [1H, tt, J=8.1 and 4.5, (CH$_2$)$_2$CH], 2.99 (2H, apparent d, J=12.1, 2×NCH$_A$H$_B$), 6.48 (1H, s, N=C—CH=C), 7.44 (2H, d, J=8.6, 2×ArH o to Cl; and 7.79 (2H, d, J=8.6, 2×ArH m to Cl); δ$_C$ (90 MHz; d$_6$-DMSO) 39.9 (t), 34.2 (d), 46.2 (t), 98.9 (d), 126.8 (d), 128.7 (d), 131.7 (s), 132.4 (broad, s), 147.5 (broad, s) and 151.1 (broad, s); m/z (CI$^+$, NH$_3$) 262 (M$^+$+H; 60%) and 139 (100).

c) 3-(1-(4-Chlorobenzyl)-4-piperidinyl)-5-(4-chlorophenyl)pyrazole

A solution of 3-(4-piperidinyl)-5-(4-chlorophenyl)pyrazole (1.50 g), triethylamine (1.60 cm$^3$) and 4-chlorobenzyl chloride (0.92 g) in 3:1 dichloromethane-dimethylformamide (20 cm$^3$) was stirred at room temperature for 4.5 hours. Dichloromethane was removed by evaporation and the crude product was partitioned between water (25 cm$^3$) and ethyl acetate (2×25 cm$^3$). The combined organic extracts were washed with saturated brine (20 cm$^3$), dried (MgSO$_4$), filtered and evaporated to dryness to give an off-white solid. Recrystallisation from ethanol-water yielded the title compound as fine, white needles (0.575 g, 26%), m.p. 179°–181° C. (from EtOH/H$_2$O); (Found: C, 65.19; H, 5.24; N, 10.86. C$_{21}$H$_{21}$N$_3$Cl$_2$ requires C, 65.29; H, 5.48; N, 10.88%.); δ$_H$ (360 MHz; CDCl$_3$) 1.71 (2H, apparent qd, J=12 and 3, 2×NCH$_2$CH$_A$H$_B$), 1.84 (2H, apparent d, J=11, 2×NCH$_2$CH$_A$H$_B$), 1.92 (2H, apparent t, J=11, 2×NCH$_A$H$_B$), 2.41–2.55 (1H, m, NCH$_2$CH$_2$CH), 2.84 (2H, apparent d, J=11, 2×NCH$_A$H$_B$), 3.44 (2H, s, NCH$_2$Ar), 6.21 (1H, s, N=C—CH=C), 7.30–7.21 (6H, m, 6×ArH), 7.61 (2H, d J=8.1, 2×ArH) and 11.6–12.0 (1H, br s, NH); δ$_C$ (90 MHz; CDCl$_3$) 31.9 (t), 33.8 (d), 53.3 (t), 62.5 (t), 99.5 (d), 126.9 (d), 128.6 (d), 128.9 (d), 130.3 (d), 132.8 (s), 133.5 (s) and 136.8 (s). 3 quaternary carbons not observed; m/z (CI$^+$; NH$_3$) 386 ($\underline{M}^+$+H; 30%), 262 (22), 228 (18), 210 (10), 196 (17), 179 (28), 162 (28), 154 (40), 142 (67), and 140 (100); m/z (CI$^-$; NH$_3$) 420 ($\underline{M}^-$+Cl; 2%); 385 ($\underline{M}^-$; 10), 259 (10), 178 (27) and 127 (20).

EXAMPLE 10

3-(1-Benzyl-4-piperidinyl)-5-(4-chlorophenyl)pyrazole

White needles, m.p. 164°–167° C. (from EtOH/H$_2$O) (Found: C, 71.68; H, 6.30; N, 11.94. C$_{21}$H$_{22}$N$_3$Cl requires C, 71.82; H, 6.22; N, 11.72%.); δ$_H$ (360 MHz; CDCl$_3$) 1.74 (2H apparent qd, J=12 and 4, 2 ×NCH$_2$CH$_A$H$_B$), 1.86 (2H, apparent d, J=10, 2×NCH$_2$CH$_A$H$_B$), 1.97 (2H apparent t, J=11, 2×NCH$_A$H$_B$), 2.55 (1H, tt, J=11.6 and 3.8, NCH$_2$CH$_2$CH), 2.55 (2H, apparent d, J=12, 2×NCH$_A$H$_B$), 3.50 (2H, br s, NCH$_2$Ph), 6.29 (1H, s, N=C—CH=C), 7.18–7.38 (7H, m, 2×ArH and Ph) and 7.61 (2H, d, J=8.3, 2×ArH); δ$_C$ (90 MHz; CDCl$_3$) 32.0 (t), 33.9 (d), 53.4 (t), 63.3 (t), 99.5 (d), 126.9 (d), 127.1 (d), 128.2 (d), 128.9 (d), 129.2 (d), 133.5 (s) and 138.1 (s). Three quaternary carbons not observed; m/z (CI$^+$, NH$_3$) 352 (M$^+$+H; 85%), 318 (18), 262 (21), 179 (22), 162 (25), 154 (30), 127 (35), 125 (55) and 106 (100); m/z (CI$^-$, NH$_3$) 386 (M$^-$+Cl; 2%), 351 (M$^-$; 11), 259 (10), 178 (60) and 81 (100).

EXAMPLE 11

3-(1-(4-Methylbenzyl)-4-piperidinyl)-5-(4-chlorophenyl)pyrazole

White needles, m.p. 181°–183° C. (from EtOH-H$_2$O) (Found C, 72.37; H, 6.56; N, 11.65. C$_{22}$H$_{24}$N$_3$Cl requires C, 72.22; H, 6.61; N, 11.48%); $\delta_H$ (360 MHz; CDCl$_3$) 1.80 (2H, apparent qd, J=12 and 1, 2×NCH$_2$CH$_A$H$_B$), 1.94 (2H, apparent d, J=12, 2×NCH$_2$CH$_A$H$_B$), 2.08 (2H, apparent t, J=11, 2×NCH$_A$H$_B$), 2.34 (3H, s, CH$_3$), 2.62–2.72 (1H, m, NCH$_2$CH$_2$CH), 2.96 (2H apparent d, J=11, 2×NCH$_A$H$_B$), 3.50 (2H, s, NCH$_2$Ar), 6.32 (1H, s, N=C—CH=C), 7.13 (2H, d, J=7.8, 2×ArH o to Me), 7.22 (2H, d, J=7.8, 2×ArH m to Me), 7.33 (2H, d, J=8.3, 2×ArH o to Cl), 7.67 (2H, d, J=8.3, 2×ArH m to Cl) and 11.20–11.60 (1H, br s, NH); $\delta_C$ (90 MHz; CDCl$_3$) 21.1 (q). 32.0 (t), 34.0 (d), 53.4 (t) 63.0 (t), 99.2 (d), 126.8 (d), 128.7 (d), 128.9 (d), 129.2 (d) 133.1 (s) and 136.6 (s). Four quaternary carbons not observed; m/z (CI$^+$, NH$_3$) 366 (M$^+$+H; 40%) 262 (12), 179 (13), 154 (22), 139 (30), 126 (41) and 120 (100); m/z (CI$^-$, NH$_3$) 400 (M$^-$+Cl; 5%), 365 (M$^-$; 11), 259 (19), 178 (70) and 81 (100).

EXAMPLE 12

3-(1-(4-Methoxybenzyl)-4-piperidinyl)-5-(4-chlorophenyl)pyrazole

Fine, cream coloured needles, m.p. 166°–168° C. (from EtOH/H$_2$O) (Found C, 69.49; H, 6.51; N, 11.13. C$_{22}$H$_{24}$N$_3$OCl requires C, 69.19; H, 6.33; N, 11.00%); $\delta_H$ (360 MHz, CDCl$_3$) 1.74 (2H, apparent qd, J=12 and 3, 2×NCH$_2$CH$_A$H$_B$), 1.84–1.97 (4H, m, 2×NCH$_2$CH$_A$H$_B$ and 2×NCH$_A$H$_B$), 2.55 (1H, tt, J 12 and 4, NCH$_2$CH$_2$CH), 2.90 (2H, apparent d, J=11, 2×NCH$_A$H$_B$), 3.44 (2H, s, NCH$_2$Ar), 3.80 (3H, s, OCH$_3$), 6.30 (1H, s, N=C—CH=C), 6.85 (2H, s, J=8.5, 2×ArH o to OMe), 7.21 (2H, d, J=8.5, 2×ArH m to OMe) 7.31 (2H, d, J=8.3, 2×ArH o to Cl) and 7.61 (2H, d, J=8.3, 2×ArH m to Cl); $\delta_C$ (90 MHz; CDCl$_3$) 32.0 (t), 34.0 (d), 53.3 (t), 55.2 (q), 62.7 (t), 99.5 (d), 113.6 (d), 126.9 (d), 128.8 (d), 130.1 (s), 130.4 (d), 131.4 (s), 133.5 (s) and 158.7 (s). Two quaternary carbons not observed; m/z (CI$^+$, NH$_3$) 382 (M$^+$+H; 20%) 262 (17), 179 (18), 154 (39) and 136 (100); m/z (CI$^-$, NH$_3$) 416 (M$^-$+Cl; trace), 381 (M$^-$; 5), 259 (40) and 178 (100).

EXAMPLE 13

3-(1-(2-Propenyl)-4-piperidinyl)-5-(4-chlorophenyl)pyrazole

White granules, m.p. 165°–167° C. (from EtOH/H$_2$O) (Found: C, 67.65; H, 6.68; N, 13.92. C$_{17}$H$_{20}$N$_3$Cl requires C, 67.51; H, 6.79; N, 13.83%.); $\delta_H$ (360 MHz; CDCl$_3$) 1.79 (2H, apparent qd, J=12 and 3, 2×NCH$_2$CH$_A$H$_B$), 1.97–2.08 (4H, m, 2×NCH$_2$CH$_A$H$_B$ and 2×NCH$_A$H$_B$), 2.67 (1H, tt, J=11.6 and 3.9, NCH$_2$CH$_2$CH), 2.98–3.02 (4H, m, 2×NCH$_A$H$_B$ and NCH$_2$CH=CH$_2$), 5.15 (1H, d, J=10, CH=CH$_A$H$_B$, 5.19 (1H, d, J=17, CH=CH$_A$H$_B$), 5.88 (1H, ddt, J=17, 10 and 6.5, CH=CH$_2$), 6.31 (1H, s, N=CCH), 7.32 (2H, d, J=8.5, 2×ArH o to Cl); and 7.69 (2H, d, J=8.5, 2×ArH m to Cl); $\delta_C$ (90 MHz; CDCl$_3$) 31.9 (t), 33.9 (d), 53.4 (t), 61.8 (t), 98.9 (d), 117.7 (t), 126.7 (d), 128.6 (d), 131.6 (s), 132.9 (s) and 135.2 (d). 2×s not observed; m/z (CI$^+$; NH$_3$) 302 (M$^+$+H; 100%); m/z (CI$^-$; NH$_3$) 336 (M$^-$+Cl; 10%), 301 (M$^-$; 21) and 178 (100).

EXAMPLE 14

3-(1-(4-Nitrobenzyl)-4-piperidinyl)-5-(4-chlorophenyl)pyrazole

Yellow granules, m.p. 187°–190° C. (from EtOH/H$_2$O) (Found: C, 63.67, H, 5.28; N, 14.21. C$_{21}$H$_{21}$N$_4$O$_2$Cl requires C, 63.55; H, 5.33; N, 14.12%); $\delta_H$ (360 MHz; CDCl$_3$) 1.52 (2H, apparent q, J=12, 2×NCH$_2$CH$_A$H$_B$), 1.71 (2H, apparent d, J=12, 2×NCH$_2$CH$_A$H$_B$), 1.89 (2H, apparent t, J=11, 2×NCH$_A$H$_B$), 2.43 (1H, apparent t, J=12, NCH$_2$CH$_2$CH), 2.64 (2H, apparent d, J=11, 2×NCH$_A$H$_B$) 3.35 (2H, s, NCH$_2$Ar), 6.05 (1H, s, N=C—CH=C), 7.05 (2H, d, J=8.3, 2×ArH m to nitro), 7.28 (2H, d, J=8.3, 2×ArH o to Cl), 7.43 (2H, d, J=8.3, 2×ArH m to Cl), 7.88 (2H, d, J=8.3, 2×ArH o to nitro) and 12.12 (1H, br s, NH); $\delta_C$ (90 MHz; CDCl$_3$) 3.17 (t), 33.6 (d), 53.4 (t), 62.0 (t) 98.9 (d), 123.1 (d), 126.5 (d), 128.4 (d), 129.2 (d), 132.4 (s) and 146.7 (s). Four quaternary carbons not observed; m/z (CI$^+$, NH$_3$) 397 (M$^+$+ H; 10%) 262 (60) and 139 (100); m/z (CI$^-$, NH$_3$) 396 (M$^-$; 20%) 255 (20) 151 (50) and 79 (100).

EXAMPLE 15

3-(1-(4-Chlorobenzyl)-4-piperidinyl)-5-phenylpyrazole

Chunky white needles m.p. 183° C. (from EtOH/H$_2$O) (Found C, 72.03; H, 6.27; N, 12.10. C$_{21}$H$_{22}$ClN$_3$ requires C, 71.68; H, 6.30; N, 11.94%); $\delta_H$ (360 MHz, d$_6$-DMSO) 1.66 (2H, dq, J=3.3 and 12.2, CH$_A$H$_B$CH), 1.89 (2H, br d, J=12.0, CH$_A$H$_B$CH), 2.06 (2H, dt, J=2.2 and 11.6, CH$_A$H$_B$N), 2.64 (1H, br m, CH$_2$CH), 2.85 (2H, br d, J=11.5, CH$_A$H$_B$N), 3.48 (2H, CH$_2$Ar), 6.48 (1H, br s, CCHC), 7.26 (1H, br t, J=7, Ph-4-H), 7.34 (2H, d, J=8.5, CH$_2$ArH), 7.39 (2H, d, J=8.5, CH$_2$ArH), 7.4 (2H, br m, Ph-3-H), 7.75 (2H, br d, J=7, Ph-2-H), 12.59 and 12.88 (1H, br s and br s, N$_A$N$_B$H and N$_A$HN$_B$ tautomers); m/z (CI$^+$, NH$_3$) 352 (M+1).

EXAMPLE 16

3-(1-(4-Chlorobenzyl)-4-pipereridinyl)-5-(2-thienyl)pyrazole

Pale yellow needles m.p. 177°–178° C. (from EtOH/H$_2$O) (Found C, 63.87; H, 5.59; N, 11.78. C$_{19}$H$_{20}$ClN$_3$S requires C, 63.76; H, 5.63; N, 11.74%); $\delta_H$ (360 MHz, d$_6$-DMSO) 1.65 (2H, dq, J=3.1 and 12.1, CH$_A$H$_B$CH), 1.88 (2H, br d, J=11.0, CH$_A$H$_B$CH), 2.05 (2H, dt, J=2.2 and 11.7 Hz CH$_A$H$_B$N), 2.64 (1H, br m, CH$_2$CH), 2.84 (2H, br d, J=11.5, CH$_A$H$_B$N), 3.48 (2H, s, ArCH$_2$), 6.36 (1H, br s, CCHC), 7.05 (1H, m, thiophene-4-H), 7.31 (1H, m thiophene-H), 7.34 (2H, d, J=8.6, CH$_2$ArH), 7.38 (2H, d, J=8.6, CH$_2$ArH), 7.4 (1H, m, thiophene-H), 12.55 and 12.89 (1H, br s and br s, N$_A$N$_B$H and N$_A$HN$_B$ tautomers; m/z (CI$^+$, NH$_3$) 358 (M+1)

EXAMPLE 17

3-(1-(4-Chlorophenyl)-4-piperidinyl)-5-(4-isopronylphenyl)pyrazole

Fine white needles, m.p. 167°–168° C. (from Ether/hexane) (Found C, 73.53; H, 7.07; N, 10.78. C$_{24}$H$_{28}$ClN$_3$ requires (C, 73.17; H, 7.16; N, 10.67%); $\delta_H$ (360 MHz, d$_6$-DMSO) 1.21 (6H, d, J=6.9, (CH$_3$)$_2$) 1.66 (2H, dq, J=3 and 11.9, CH$_A$H$_B$CH) 1.88 (2H, br d, J=11.8, CH$_A$H$_B$CH), 2.06 (2H, dr, J=2.2 and 11.7, CH$_A$H$_B$N), 2.62 (1H, br m, CH$_2$CH), 2.83–2.92 (3H, m, CH$_A$H$_B$N and CH(CH$_3$)$_2$), 3.47 (2H, s, ArCH$_2$) 6.43 (1H, br s, CCHC), 7.26 (2H, br m ArH), 7.34 (2H, d, J=8.6, CH$_2$ArH), 7.39 (2H, d, J=8.6, CH$_2$ArH), 7.65 (2H, br m, ArH), 12.52 and 12.80 (1H, br s and br s, $N_AN_BH$ and $N_AHN_B$ tautomers); m/z (CI$^+$, NH$_3$) 394 (M$^+$+1)

EXAMPLE 18

3-(1-(4-Chlorobenzyl)-1-piperidinyl)-5-(4-methoxyphenyl) pyrazole

White crystalline solid, m.p. 163° C. and 172° C. (from Ethyl acetate). Two crystal forms exist over the temperature range. (Found C, 69.19; H, 6.33; N, 11.00. $C_{22}H_{24}ClN_3O$ requires C, 69.58; H, 6.35; N, 11.08%); $\delta_H$ (360 MHz, CDCl$_3$) 1.82 (2H, dq, J=3.4 and 12.1, CH$_A$H$_B$CH) 1.97 (2H, br d, J=11.6, CH$_A$H$_B$CH), 2.08 (2H, br t, J=10.8, CH$_A$H$_B$N) 2.64–2.72 (1H, m, CH$_2$CH), 2.95 (2H, br d, J=11.7, CH$_A$H$_B$N), 3.51 (2H, s, ArCH$_2$), 3.83 (3H, s, CH$_3$), 6.29 (1H, s CCHC), 6.92 (2H, dt, J=8.8 and 2.5, ArH o to OMe), 7.23 (4H, s, CH$_2$ ArH), 7.60 (2H, br d, J=8.5, ArH m to OMe); m/z (CI$^+$, NH$_3$) 382 (M$^+$+1).

EXAMPLE 19

3-(1-Cyclohexylmethyl-4-piperidinyl)-5-(4-chlorophenyl)pyrazole

White granules, m.p. 186°–187° C. (from EtOH/H$_2$O/Me$_2$CO) (Found: C, 70.27; H, 7.89; N, 11.70. $C_{21}H_{28}N_3Cl$ requires C, 70.47; H, 7.88; N, 11.74%); $\delta_H$ (360 MHz; CDCl$_3$) 0.88 (2H, apparent q, J=11.6, CH$_2$), 1.10–1.29 (3H, m, methylenes), 1.47–1.53 (1H, m, NCH$_2$CH), 1.69–1.99 (11H, m, methylenes), 2.14 (2H, d, J=7.0, NCH$_2$CH), 2.62 (1H, tt, J=11.5 and 3.9, NCH$_2$CH$_2$CH), 2.93 (2H, apparent d, J=11, 2×NCH$_A$H$_B$), 6.33 (1H, s, N=CCH), 7.33 (2H, d, J=8.4, 2×ArH o to Cl) and 7.65 (2H, d, J=8.3, 2×ArH m to Cl); $\delta_C$ (90 MHz; CDCl$_3$) 26.1 (t), 26.8 (t), 32.0 (t), 32.04 (t), 34.1 (d), 35.2 (d), 54.1 (t), 66.0 (t), 99.6 (d), 126.9 (d), 128.8 (d) and 133.5 (s). 3×s not observed; m/z (CI$^+$; NH$_3$) 358 (M$^+$+H; 100%); m/z (CI$^-$; NH$_3$) 392 (M$^-$+Cl; 32%), 357 (M$^-$; 18), 242 (5), 178 (37) and 127 (100).

EXAMPLE 20

3-(1-(2-Phenylethyl)-4-piperidinyl)-5-(4-chlorophenyl)pyrazole

Beige granules, m.p. 169°–171° C. (from EtOH/H$_2$O) (Found: C, 72.09; H, 6.48; N, 11.50. $C_{22}H_{24}N_3Cl$ requires C, 72.22; H, 6.61; N, 11.48%); $\delta_H$ (360 MHz; CDCl$_3$) 1.83 (2H, apparent qd, J=12 and 4, 2×NCH$_2$CH$_A$H$_B$), 2.00 (2H, apparent d, J=11, 2×NCH$_2$CH$_A$H$_B$), 2.14 (2H, apparent t, J=12, 2×NCH$_A$H$_B$), 2.61–2.65 (2H, m, NCH$_2$CH$_2$Ar), 2.70 (1H, tt, J=11.8 and 3.9, NCH$_2$CH$_2$CH), 2.81–2.86 (2H, m, NCH$_2$CH$_2$Ar), 3.08 (2H, apparent d, J=12, 2×NCH$_A$H$_B$), 6.34 (1H, s, N=CCH=C), 7.35–7.16 (7H, m, Ph and 2×ArH o to Cl) and 7.69 (2H, d, J=8.4, 2×ArH m to Cl); $\delta_C$ (90 MHz; CDCl$_3$) 32.0 (t), 33.6 (t), 34.0 (d), 53.6 (t), 60.8 (t), 99.1 (d), 126.0 (d), 126.8 (d), 128.3 (d), 128.65 (d), 1228.70 (d), 133.1 (s) and 140.3 (s). 3×s is not observed; m/z (CI$^+$; NH$_3$) 366 (M$^3$+H; 100%); m/z (CI$^-$; NH$_3$) 400 (M$^-$+Cl; 5%), 365 (M$^-$; 12) and 178 (100).

EXAMPLE 21

3-(1-(3,4-Dichlorobenzyl)-4-piperidinyl)-5-(4-chlorophenyl)pyrazole

White needles, m.p. 171°–174° C. (from EtOH/EtOAc/H$_2$O) (Found: C, 59.95; H, 4.66; N, 9.82. $C_{21}H_{20}N_3Cl_3$ requires C, 59.95; H, 4.79; N, 9.99%); $\delta_H$ (360 MHz; CDCl$_3$+d$_6$-DMSO) 1.78 (2H, apparent qd, J=12 and 4, 2×NCH$_2$CH$_A$H$_B$), 1.97 (2H, apparent d, J=12, 2×NCH$_2$CH$_A$H$_B$), 2.11 (2H, apparent t, J=12, 2×NCH$_A$H$_B$), 2.69 (1H, tt, J=12 and 4, NCH$_2$CH$_2$CH), 2.91 (2H, apparent d, J=12, 2×NCH$_{AB}$), 3.47 (2H, s, NCH$_2$Ar), 6.32 (1H, s, N=C—CH=C), 7.19 (1H, dd, J 8.1 and 1.6, H-5), 7.32 (2H, d, J=8.6, 2×ArH o to Cl), 7.38 (1H, d, J=8.1, H-6), 7.46 (1H, d, J=1.6, H-2) and 7.71 (2H, d, J=8.6, 2×ArH m to Cl); $\delta_C$ (90 MHz; CDCl$_3$+d$_6$-DMSO) 36.7 (t), 38.6 (d), 58.3 (t) 66.6 (t), 103.6 (d), 131.4 (d), 133.0 (d), 133.3 (d), 134.8 (d), 135.2 (s), 135.3 (d) 136.6 (s), 136.7 (s), 137.5 (s), 144.2 (s) and 152.7 (s). One quaternary carbon not observed; m/z (CI$^+$, NH$_3$) 420 (M$^+$+H; 30%), 386 (12), 287 (90), 262 (46), 190 (47), 140 (60) and 100 (100); m/z (CI$^+$, NH$_3$) 419 (M$^-$; 20%), 259 (10), 178 (21) and 79 (100).

EXAMPLE 22

3-(1-(4-Chlorobenzyl)-4-piperidinyl)-5-(3-chlorophenyl)pyrazole

White needles, m.p. 156°–157° C. (from EtOH/H$_2$O) (Found C, 65.23; H, 5.43; N, 10.70. $C_{21}H_{21}Cl_2N_3$ requires C, 65.29; H, 5.48; N, 10.88%); $\delta_H$ (360 MHz,d$_6$-DMSO) 1.66 (2H, dq, J=3.1 and 12.0, CH$_A$H$_B$CH), 1.89 (2H, br d, J=11.4, CH$_A$H$_B$CH), 2.06 (2H, dt, J=2.2 and 11.7, CH$_A$H$_B$N), 2.57–2.72 (1H, br m, CH$_2$CH), 2.85 (2H, br d, J=11.5, CH$_A$H$_B$N), 3.48 (2H, s, CH$_2$Ar), 6.58 (1H, br s, CCHC), 7.34 (2H, d, J=8.5, CH$_2$ArH), 7.39 (2H, d, J=8.5, CH$_2$ArH), 7.32–7.44 (2H, m, ArH), 7.72 (1H, br d, J=7.5, ArH p to Cl), 7.80 (1H, t, J=1.7, ArH o to Cl and to pyrazole), 12.73 and 12.98 (1H, br s and br s, $N_AN_BH$ and $N_AHN_B$ tautomers); m/z (CI$^+$, NH$_3$) 386 (M$^+$+1).

EXAMPLE 23

3-(1-(3-Chlorobenzyl)-4-piperidinyl)-5-(4-chlorophenyl)pyrazole

White granules, m.p. 134°–136° C. (from EtOH/H$_2$O) (Found: C, 65.28; H, 5.41; N, 10.86. $C_{21}H_{21}N_3Cl_2$ requires C, 65.29; H, 5.48; N, 10.88%); $\delta_H$ (360 MHz; CDCl$_3$) 1.74 (2H, apparent qd, J=12 and 4, 2×NCH$_2$CH$_A$H$_B$CH), 1.87 (2H, apparent d, J=12, 2×NCH$_2$CH$_A$H$_B$), 1.97 (2H, apparent t, J=12, 2×NCH$_A$H$_B$), 2.56 (1H, tt, J=12 and 4, NCH$_2$CH$_2$CH), 2.87 (2H, apparent d, J=12, 2×NCH$_A$H$_B$), 3.46 (2H, s, NCH$_2$Ar), 6.31 (1H, s, N=C—CH=C), 7.17–7.33 (6H, m, 6×ArH), 7.62 (2H, d, J 8.4, 2×ArH m to Cl) and 10.07 (1H, br s, NH); $\delta_C$ (90 MHz; CDCl$_3$) 32.0 (t), 33.8 (d), 53.4 (t), 62.6 (t), 99.6 (d), 126.9 (d), 127.1 (d), 128.9 (d), 129.0 (d), 129.5 (d) 133.6 (s), 134.2 (s) and 140.5 (s). Three quaternary carbons not observed; m/z (CI$^+$, NH$_3$) 386 (M$^+$+H; 100%); m/z (CI$^-$, NH$_3$) 420 (M$^-$+Cl; 12%), 385 (M$^-$;14) and 127 (100).

EXAMPLE 24

3-(1-(4-Chlorobenzyl)-4-piperidinyl)-5-(2-chlorophenyl) pyrazole, oxalate salt

Amorphous white solid, m.p. 133°–135° C. (EtOH) (Found: C, 55.87; H, 5.00; N, 8.41. $C_{21}H_{21}Cl_2N_3.(C_2H_2O_4)$ .(H$_2$O) requires C, 55.88; H, 5.10; N, 8.50%); $\delta_H$ (360 MHz, d$_6$-DMSO) 1.85 (2H, br q, J=12, CH$_A$H$_B$CH), 2.08 (2H, br d, J=12, CH$_A$H$_B$CH), 2.76 (3H, br t, J=12, CH$_A$H$_B$N), 2.88 (1H, br m, CH$_2$CH), 3.20 (2H, br d, J=12, CH$_A$H$_B$N), 4.06 (2H, br s ArCH$_2$), 6.53 (1H, s, CCHC), 7.35 (1H, dt, J=2.0 and 7.5, ArH), 7.39 (1H, dt, J=1.6 and 7.3, ArH), 7.50 (4H, s, CH$_2$ArH), 7.53 (1H, dd, J=1.6 and 7.5, ArH), 7.71 (1H, dd, J=2.1 and 7.3, ArH o to pyrazole); m/z (CI$^+$, NH$_3$) 386 (M$^+$+H).

EXAMPLE 25

3-(1-Benzyl-4-piperidinyl)-5-phenylpyrazole

White plates, m.p. 130°–131° C. (from EtOH/H$_2$O) (Found: C, 76.80; H, 7.39; N, 12.86. C$_{21}$H$_{23}$N$_3$.(0.6H$_2$O) requires C, 76.84; H, 7.43; N, 12.80%); δ$_H$ (360 MHz, d$_6$-DMSO) 1.67 (2H, dq, J=3.2 and 12.2, CH$_A$H$_B$CH) 1.89 (2H, br d, J=11.4, CH$_A$H$_B$CH), 2.05 (2H, dt, J=2.3 and 11.7, CH$_A$H$_B$N), 2.63 (1H, br m, CH$_2$CH), 2.87 (2H, br d, J=11.6, CH$_A$H$_B$N), 3.48 (2H, s, PhCH$_2$), 6.49 (1H, br s, CCHC), 7.22–7.38 (8H, m, CH$_2$PhH and PhH), 7.75 (2H, br d, J=7, PhH o to pyrazole), 12.60 and 12.88 (1H, br s and br s, N$_A$HN$_B$ and N$_A$N$_B$H tautomers); m/z (CI$^+$, NH$_3$) 318 (M$^+$+H).

EXAMPLE 26

3-(1-(4-Chlorobenzyl)-4-piperidinyl)-5-(2-methoxyphenyl)pyrazole

Pale yellow plates, m.p. 102°–103° C. (from ether/hexane) (Found: C, 69.59; H, 6.38; N, 11.01. C$_{22}$H$_{24}$ClN$_3$O requires C, 69.19; H, 6.33; N, 11.03%) δ$_H$ (360 MHz, d$_6$-DMSO) 1.66 (2H, dq, J=3.3 and 12.2, CH$_A$H$_B$CH) 1.88 (2H, br d, J=10.7, CH$_A$H$_B$CH) 2.06 (2H, dt, J=2.1 and 11.6, CH$_A$H$_B$N), 2.61 (1H, br m, CH$_2$CH), 2.85 (2H, br d, J=11.5, CH$_A$H$_B$N), 3.47 (2H, s, ArCH$_2$), 3.86 (3H, s, CH$_3$), 6.50 (1H, s, CCHC), 6.98 (1H, br t, J=7.5 Hz ArH m to pyrazole) 7.08 (1H, br d, J=8.3, ArH o to OCH$_3$), 7.28 (1H, br t, J=7.2, ArH p to pyrazole), 7.34 (2H, dd, J=6.5 and 2.2, CH$_2$ArH), 7.38 (2H, dd, J=6.5 and 2.2, CH$_2$ArH), 7.68–7.84 (1H, v br s, ArH o to pyrazole), 12.51 (1H, br s, NH); m/z (CI$^+$, NH$_3$) 382 (M$^+$+H).

EXAMPLE 27

3-(1-(2-Methylbenzyl)-4-piperidinyl)-5-(4-chlorophenyl)pyrazole

Fine, white needles, m.p. 142°–143° C. (from ethanol/water) (Found: C, 72.56; H, 6.57; N, 11.71. C$_{22}$H$_{24}$N$_3$Cl requires C, 72.22; H, 6.61; N, 11.48%); δ$_H$ (360 MHz, d$_6$-DMSO), 1.58–1.69 (2H, dq, J=3.1 and 12, CH$_A$H$_B$CH), 1.86–1.89 (2H, br d, J=12, CH$_A$H$_B$CH), 2.05–2.11 (2H, dt, J=3.1 and 11, CH$_A$H$_B$N), 2.33 (3H, s, CH$_3$), 2.65 (1H, m, CHCH$_2$) 2.84–2.87 (2H, d, J=11, CH$_A$H$_B$N), 3.43 (2H, s, ArCH$_2$), 6.51 (1H, s, CCHC), 7.12–7.25 (4H, m, CH$_2$ArH), 7.42–7.44 (2H, d, J=7.8, CArH), 7.76–7.78 (2H, d, J=7.8, CArH), 12.68 (1H, br s, NH); m/z (CI$^+$, NH$_3$) 366 (3+H).

EXAMPLE 28

3-(1-(3-Nitrobenzyl)-4-piperidinyl)-5-(4-chlorophenyl)pyrazole

Fine, pale yellow needles, m.p. 174°–176° C. (from ethanol/water) (Found: C, 63.85; H, 5.31; N, 14.10. C$_{21}$H$_{21}$N$_4$O$_2$Cl requires C, 63.55; H, 5.33; N, 14.12%); δ$_H$ (360 MHz, d$_6$-DMSO) 1.69 (2H, dq, J=2.8 and 12, CH$_A$H$_B$CH), 1.90 (2H, br d, J=12, CH$_A$H$_B$CH), 2.13 (2H, dt, J=2.1 and 10, CH$_A$H$_B$N), 2.6–2.8(1H, m, CHCH$_2$) 2.88 (2H, br d, J=10, CH$_A$H$_B$N), 3.64 (2H, s CH$_2$Ar), 6.53 (1H, br s, CCHC), 7.43 (2H, d, J=7.5, CArH), 7.64 (1H, t, J=7.5, ArH, m to NO$_2$), 7.77–7.80 (3H, m, CArH and ArH p to NO$_2$), 8.12–8.14 (1H, dd, J=1.4 and 7.5, ArH p to CH2), 8.18 (1H, br s, ArH m to NO$_2$ and CH$_2$), 12.69 (1H, br s, NH), m/z (CI$^+$, NH$_3$) 397 (M$^+$+H).

EXAMPLE 29

3-(1-(3-Methylbenzyl)-4-piperidinyl)-5-(4-chlorophenyl)pyrazole

Fine, white crystalline solid, m.p. 119°–120° C. (from ethanol/water) (Found: C, 72.63; H, 6.55; N, 11.50, C$_{22}$H$_{24}$N$_3$Cl requires C, 72.22, H, 6.61; N, 11.48%); δ$_H$ (360 MHz, d$_6$-DMSO), 1.61–1.71 (2H, dq, J=3.6 and 12, CH$_A$H$_B$CH), 1.86–1.89 (2H, br d, J=12, CH$_A$H$_B$C), 2.00–2.06 (2H, dt, J=3.6 and 10, CH$_A$H$_B$N), 2.30 (3H, s, CH$_3$), 2.63 (1H, br m, CHCH$_2$), 2.85–2.88 (2H, br d, J=10, CH$_A$H$_B$N), 3.43 (2H, s, CH$_2$Ar), 6.52 (1H, s, CCHC), 7.05–7.12 (3H, m, CH$_2$ArH), 7.19 (1H, t, J=7.4, ArH m to CH$_3$), 7.42 (2H, d, J=8.0 Hz CArH), 7.76 (2H, d, J=8.0, CArH), 12.68 (1H, br s, NH); m/z (CI$^+$, NH$_3$) 366 (M$^+$+H).

EXAMPLE 30

3-(1-(2-Nitrobenzyl)-4-piperidinyl)-5-(4-chlorophenyl)pyrazole

Fine, pale yellow needles, m.p. 150°–151° C. (from ethanol/water) (Found: C, 63.61; H, 5.19; N, 14.03. C$_{21}$H$_{21}$N$_4$O$_2$Cl requires C, 63.55; H, 5.33; N, 14.12%); δ$_H$ (360 MHz, d$_6$-DMSO), 1.63 (2H, dq, J=2.9 and 11, CH$_A$H$_B$CH), 1.88 (2H, br d, J=11, CH$_A$H$_B$CH), 2.15 (2H, dt, J=2.2 and 11, CH$_A$H$_B$N), 2.63 (1H, m, CHCH), 2.76 (2H, br d, J=11, CH$_A$H$_B$N), 3.74 (2H, s, CH$_2$Ar), 6.51 (1H, br s, CCHC), 7.44 (2H, d, J=7.2, CArH), 7.54 (1H, dt, J=2.4 and 8.3, ArH p to NO$_2$ and m to CH$_2$), 7.63–7.69 (2H, m, ArH m to NO$_2$ and o to CH$_2$, ArH p to NO$_2$), 7.79 (2H, d J=7.2, CArH), 7.87 (1H, d, J=7.8, ArH, o to NO$_2$), 12.67 (1H, s, NH); m/z (CI$^+$, NH$_3$) 397 (M$^+$+H).

EXAMPLE 31

3-(1-(2-Chlorobenzyl)-4-piperidinyl)-5-(4-chlorophenyl)pyrazole

Fine, pale yellow crystals, m.p. 137°–139° C. (from ethanol/water) (Found: C, 65.19; H, 5.52; N, 10.87. C$_{21}$H$_{21}$N$_3$Cl$_2$ requires C, 65.29; H, 5.48; N, 10.88%); δ$_H$ (360 MHz, d$_6$-DMSO), 1.74 (2H, dq, J=3.5 and 12, CH$_A$H$_B$CH$_2$), 1.92 (2H, br d, J=12, CH$_A$H$_B$CH$_2$), 2.19 (2H, dt, J=3.5 and 11, CH$_A$H$_B$N), 2.67 (1H, m, CHCH$_2$) 2.91 (2H, br d, J=12, CH$_A$H$_B$N) 3.58 (2H, s, ArCH$_2$), 6.53 (1H, s, CCHC), 7.26–7.36 (2H, m, ArH p to Cl, ArH m to Cl and p to CH$_2$), 7.42–7.44 (3H, m, CArH, CH$_2$ArH), 7.52 (1H, dd, J=2 and 7, CH$_2$ArH), 7.76–7.80 (2H, d, J=8, CArH), 12.69 (1H, br s, NH); m/z (CI$^+$, NH$_3$) 386 (M$^+$+H).

EXAMPLE 32

3-(1-Cyclopropylmethyl-4-piperidinyl)-5-(4-chlorophenyl)pyrazole

White needles, m.p. 176°–178° C. (from ethyl acetate) (Found: C, 68.72; H, 6.75; N, 13.47. C$_{22}$H$_{18}$N$_3$Cl requires C, 68.45; H, 7.02;, N, 13.30%); δ$_H$ (360 MHz, d$_6$-DMSO), 0.02–0.10 (2H, m, CHCH$_A$H$_B$CH$_A$H$_B$), 0.44–0.49 (2H, m, CHCH$_A$H$_B$CH$_A$H$_B$), 0.82–0.86 (1H, m, CH$_2$CHCH$_2$), 1.71 (2H, dq, J=3 and 12, CH$_A$H$_B$CH$_2$), 1.91 (2H, br d, J=12, CH$_A$H$_B$CH$_2$), 2.04 (2H, dt, J=3 and 12, CH$_A$H$_B$N), 2.20 (2H, d, J=7, NCH$_2$CH), 2.61 (1H, m, CCHCH$_2$), 6.51 (1H, s, CCHC), 7.45 (2H, d, J=8, ArH), 7.79 (2H, d, J=8, ArH), 12.76 (1H, s, NH); m/z (CI$^+$, NH$_3$) 316 (M$^+$+H).

EXAMPLE 33

3-(1-(2-Naphthylmethyl)-4-piperidinyl)-5-(4-chlorophenyl)pyrazole

Off-white needles, m.p.180°–181° C. (from ethanol) (Found: C, 74.92; H, 6.12; N, 10.57. $C_{25}H_{24}N_3Cl$ requires C, 74.71; H, 6.02; N, 10.45%); $\delta_H$ (360 MHz, $d_6$-DMSO) 1.74 (2H, dq, J=11, $CH_AH_BCH_2$), 1.91 (2H, br d, J=11, $CH_AH_BCH_2$), 2.14 (2H, t, J=12, $CH_AH_BN$), 2.66 (1H, br m, $CH_2CH$), 2.93 (2H, br d, J=12, $CH_AH_BN$), 3.65 (2H, s, $CH_2Ar$), 6.52 (1H, s, CCHC) 7.41–7.53 (5H, m, ArH), 7.77–7.90 (6H, m, ArH), 12.68 (1H, br s, NH); m/z (CI$^+$, NH$_3$) 402 (M$^+$+H).

EXAMPLE 34

3-(1-(3-Phenyl-1-propyl)-4-piperidinyl)-5-(4-chlorophenyl)pyrazole

Fine white crystals, m.p. 165°–167° C. (from ethanol) (Found: C, 72.83; H, 6.88; N, 11.23. $C_{23}H_{26}N_3Cl$ requires C, 72.71; H, 6.90; N, 11.06%); $\delta_H$ (360 MHz, $d_6$-DMSO), 1.61–1.78 (4H, m, $CH_AH_BCH$, $CH_2CH_2CH_2$), 1.91 (2H, br d, J=12, $CH_AH_BCH_2$), 1.99 (2H, t, J=12, $CH_AH_BN$), 2.31 (2H, t, J=7, $CH_2CH_2CH_2$), 2.61 (2H, t, J=7, $CH_2CH_2CH_2$), 2.92 (2H, br d, J=12, $CH_AH_BN$), 6.51 (1H, s, CCHC), 7.14–7.22 (5H, m, $CH_2ArH$), 7.44 (2H, d, J=7, CArH), 7.79 (2H, d, J=7, CArH), 12.67 (1H, s, NH); m/z (CI$^+$, NH$_3$) 380 (M$^+$+H).

EXAMPLE 35

3-(1-(3-Methoxybenzyl)-4-piperidinyl)-5-(4-chlorophenyl)pyrazole

Fine, white crystals, m.p. 50°–52° C. (from DMF/water) (Found: C, 68.42; H, 6.42; N, 10.98. $C_{22}H_{24}N_3OCl$. (0.25H$_2$O) requires C, 68.38; H, 6.39; N, 10.87%); $\delta_H$ (360 MHz, $d_6$-DMSO), 1.71 (2H, dq, J=12, $CH_AH_BCH$), 1.90 (2H, br d, J=12, $CH_AH_BCH$), 2.07 (2H, t, J=12, $CH_AH_BN$) 2.64 (1H, br m, $CH_2CH$), 2.88 (2H, br d, J=12, $CH_AH_BN$), 3.46 (2H, s, ArCH$_2$), 3.75 (3H, s, OCH$_3$), 6.52 (1H, s, CCHC), 6.83 (1H, d, J=9, $CH_2ArH$), 6.90 (2H, m, $CH_2ArH$), 7.26 (1H, t, J=9, $CH_2ArH$ m to MeO), 7.44 (2H, d, J=8, CArH), 7.78 (2H, d, J=8, CArH), 12.68 (1H, s, NH); m/z (CI$^+$, NH$_3$) 382 (M$^+$+H).

EXAMPLES 36 & 37

5-(1-(4-Chlorobenzyl)-4-piperidinyl)-3-(4-chlorophenyl)isoxazole and 3-(1-(4-Chlorobenzyl)-4-piperidinyl)-5-(4-chlorophenyl)isoxazole Hydroxylamine hydrochloride (139 mg) was added to 1-(4-chlorobenzyl)-4-(3-hydroxy-1-oxo-3-(4-chlorophenyl) prop-2-en-1-yl)piperidine obtained from Example 1 (399 mg) and ethyldiisopropylamine (0.35 ml) in methanol (5 ml) and DMF (2 ml). After stirring for 16 h hydroxylamine hydrochloride (139 mg) and ethyldiisopropylamine (0.35 ml) were added and the mixture stirred at 50° C. for 4 h. Water (50 ml) was added, the mixture extracted with ethyl acetate (3×25 ml) and the combined organic layers washed with water and brine, dried (MgSO$_4$), evaporated in vacuo, and purified by flash chromatography, eluting with dichloromethane:methanol:triethylamine (96:4:1 v/v) to give a mixture of 5-(1-(4-chlorobenzyl)-4-piperidinyl)-3-(4-chlorophenyl)-3-hydroxy-3,4-dihydroisoxazole and 3-(1-(4-chlorobenzyl)-4-piperidinyl)-5-(4-chlorophenyl)-3-hydroxy-3,4-dihydroisoxazole (287 mg). 209 mg of this oil was dissolved in dichloromethane (5 ml), cooled to 0° C., and triethylamine (161 mg) and methanesulphonyl chloride (81 mg) added. After 1 h ethyl acetate (25mg) was added, and the mixture washed with water and brine, dried (MgSO$_4$), and evaporated in vacuo, and purified by preparative thin layer chromatography, eluting with dichloromethane:methanol:triethylamine (97:3:1 v/v) to give 5-(1-(4-chlorobenzyl)-4-piperidinyl)-3-(4-chlorophenyl) isoxazole (107 mg); oxalate salt: amorphous white solid, m.p.227°–230° C. (from ethanol) (Found: C, 58.91; H, 4.95; N, 6.15%. $C_{21}H_{20}N_2OCl_2$. (0.8$C_2H_2O_4$) requires C, 59.09; H, 4.74; N, 6.10%); $\delta_H$ (360 MHz, $d_6$-DMSO) 1.7–1.8 (2H, m, $CHCH_AH_B$), 2.08 (2H, d, J=11, $CHCH_AH_B$), 2.3–2.4 (2H, m, $NCH_AH_B$), 3.0–3.1 (3H, m, $NCH_AH_B$ and $CH_2CH$), 3.82 (2H, s, ArCH$_2$), 6.92 (1H, s, CHCO), 7.4–7.5 (4H, m, ArHCH$_2$), 7.59 (2H, d, J=8, ArH), 7.88 (2H, d, J=8, ArH); m/z (CI$^+$, NH$_3$) 387 (M$^+$+H); and 3-(1-(4-chlorobenzyl)-4-piperidinyl)-5-(4-chlorophenyl)isoxazole (51 mg); oxalate salt: white plates, m.p. 240°–242° C. (from ethanol) (Found: C, 57.85; N, 4.74; H, 5.92. $C_{21}H_{20}N_2OCl_2.C_2H_2O_4$ requires C, 57.87; H, 4.64; N 5.87%); $\delta_H$ ($d_6$-DMSO) 1.8–1.9 (2H, m, $CH_AH_BCH$), 2.05 (2H, d, J=11, $CH_AH_BCH$), 2.6–2.7 (2H, m, $NCH_AH_B$), 2.9–3.0 (1H, m, $CH_2CH$), 3.1–3.2 (2H, m, $NCH_AH_B$), 3.97 (2H, s, ArCH$_2$), 7.07 (1H, s, CHCO), 7.4–7.5 (4H, m ArHCH$_2$), 7.61 (2H, d, J=8, ArH), 7.85 (2H, d, J=8, ArH); m/z (CI$^+$, NH$_3$) 387 (M$^+$+H). The isoxazole regiochemistry was proved by X-ray.

EXAMPLES 38 & 39

1-Methyl-5-(1-(4-chlorobenzyl)-4-piperidinyl)-3-(4-chlorophenyl) pyrazole and 2-Methyl-5-(1-(4-chlorobenzyl)-4-piperidinyl)-3-(4-chlorophenyl) pyrazole 1-(4-Chlorobenzyl)-4-(3-hydroxy-1-oxo-3-(4-chlorophenyl)-prop-2-en-1-yl)piperidine obtained from Example 1 (264 mg) and methyl hydrazine (62 mg) were stirred in methanol (5 ml) and DMF (2 ml) for 16 h. Water was added, the mixture extracted with ethyl acetate (3×20 ml), the combined organic layers washed with water and brine, dried (MgSO$_4$), evaporated in vacuo, and purified by preparative thin layer chromatography, eluding with dichloromethane:methanol: triethylamine (98:2:1 v/v) to give 1-methyl-5-(1-(4-chlorobenzyl)-4-piperidinyl)-3-(4-chlorophenyl)pyrazole (93 mg): oxalate salt.

White plates, m.p. 125°–127° C. (from ethanol) (Found: C, 58.61; H, 5.04; N, 8.34. $C_{24}H_{25}N_3O_4Cl_2$ requires C, 58.78; N, 5.14; N, 8.57%); $\delta_H$ (360 MHz, $d_6$-DMSO) 1.7–1.8 (2H, m, $CHCH_AH_B$), 1.99 (2H, d, J=12, $CHCH_AH_B$), 2.69 (2H, t, J=12, $NCH_AH_B$), 2.8–2.9 (1H, m, CHCH$_2$), 3.22 (2H, d, J=12, $NCH_AH_B$), 3.80 (3H, s, CH$_3$), 4.03 (2H, s, ArCH$_2$), 6.57 (1H, s, CHCN), 7.41 (2H, d, J=7, ArH, H o to Cl), 7.50 (4H, s, ArCH$_2$), 7.76 (2H, d J=7, ArH, H m to Cl), (irradiation of the methyl group at 3.80 gives a small positive NOE to the methine at 2.8–2.9 ppm); m/z (CI$^+$, NH$_3$) 400 (M$^+$+H) and 2-methyl-5-(1-(4-chlorobenzyl)-4-piperidinyl)-3-(4-chlorophenyl) pyrazole (156 mg): oxalate salt, white plates, m.p. 110°–111° C. (from ethanol) (Found: C, 58.16; H, 5.20; N, 8.53. $C_{24}H_{25}N_3O_4Cl_2$ (0.3H$_2$O) requires C, 58.14; H, 5.20; N, 8.48%); $\delta_H$ ($d_6$-DMSO) 1.8–1.9 (2H, m, $CHCH_AH_B$), 2.04 (2H, d, J=12, $CHCH_AH_B$), 2.7–2.8 (3H, m, CHCH$_2$ and $NCH_AH_B$), 3.22 (2H, d, J=12, $NCH_AH_B$), 3.78 (3H, s, CH$_3$), 4.11 (2H, s, ArCH$_2$), 6.30 (1H, s, CHCN), 7.51 (4H, s, ArCH$_2$), 7.56 (4H, s, ArH); irradiation of the methyl group at 3.78 gave a positive NOE to the signal at 7.56 ppm; m/z (CI$^+$, NH$_3$) 400 (M$^+$+H).

EXAMPLE 40

3-(1-(4-Chlorobenzyl)-4-piperidinyl)-4-methyl-5-phenylpyrazole

Long, white needles, m.p. 192°–193° C. (from EtOH) (Found: C, 72.13; H, 6.83; N, 11.51. $C_{22}H_{24}N_3Cl$ requires C, 72.22; H, 6.61; N, 11.48%); $\delta_H$ (360 MHz; CDCl$_3$) 1.82–1.98 (4H, m, 2×NCH$_2$CH$_2$), 2.06–2.22 (5H, m, 2×NCH$_A$H$_B$ and CH$_3$), 2.64–2.78 (1H, m, NCH$_2$CH$_2$CH), 3.00 (2H, apparent d, J=11, 2×NCH$_A$H$_B$), 3.53 (2H, s, NCH$_2$Ar), 7.26–7.36 (5H, m, 3 of Ph and 2×ArH o to Cl), 7.41 (2H, dd, J=7 and 7, 2×ArH m to pyrazole) and 7.54 (2H, d, J=7.6, 2×ArH m to Cl); $\delta_C$ (90 MHz; CDCl$_3$) 8.9 (q); 31.1 (t); 34.0 (d) 53.8 (t), 62.5 (t), 109.8 (s), 127.5 (d), 127.7 (d), 128.4, (d), 128.6 (d) and 130.4 (d). 5 quaternary carbons not observed; m/z (CI$^+$, NH$_3$) 366 (M$^+$+H; 100%); m/z (CI$^-$, NH$_3$) 400 (M$^-$+Cl; 5%) 364 (M$^-$–H; 30) and 242 (100).

EXAMPLE 41

3-(1-Benzyl-4-piperidinyl)-4-methyl-5-(4-chlorophenyl)pyrazole

Colourless, transparent plates, m.p. 188°–190° C. (from EtOH) (Found: C, 72.39; H, 6.65; N, 11.61. $C_{22}H_{24}N_3Cl$ requires C, 72.22; H, 6.61, N, 11.48%); $\delta_H$ (360 MHz; CDCl$_3$ +d$_6$-DMSO) 1.61 (2H, apparent d, J=12, 2×NCH$_2$CH$_A$H$_B$), 1.90 (2H, apparent q, J=12, 2×NCH$_2$CH$_A$H$_B$), 2.04–2.18 (5H, m, 2×NCH$_A$H$_B$ and CH$_3$), 2.60–2.74 (1H, m, NCH$_2$CH$_2$CH), 2.99 (2H, apparent d, J=11, 2×NCH$_A$H$_B$), 3.53 (2H, s, NCH$_2$Ar), 7.12–7.34 (7H, m, Ph and 2×ArH o to Cl), 7.54 (2H, d, J=8, 2×ArH m to Cl) and 11.98 (1H, br s, NH); $\delta_C$ (90 MHz; CDCl$_3$+d$_6$-DMSO) 9.2 (q), 31.2 (t), 34.0 (d), 53.9 (t), 63.1 (t), 110.0 (s), 126.9 (d), 128.1 (d), 128.4 (d), 128.9 (d), 129.1 (d) and 132.6 (s). Three quaternary carbons not observed; m/z (CI$^+$, NH$_3$) 366 (M$^+$+H; 60%), 332 (15), 176 (15) and 106 (100); m/z (CI$^-$, NH$_3$) 400 (M$^-$+Cl; 20%), 364 (M$^-$–H; 15), 269 (15), 192 (25) and 127 (100).

EXAMPLE 42

3-(1-(2-Phenylethyl)-4-piperidinyl)-5-(2-pyridyl)pyrazole

Orange cubes, m.p. 155°–157° C. (from ethanol) (Found: C, 75.69; H, 7.48; N, 16.88. $C_{21}H_{24}N_4$ requires C, 75.87; H, 7.28, N, 16.85%); δ(360 MHz, d$_6$-DMSO) 1.6–1.7 (2H, m, NCH$_2$CH$_A$H$_B$), 1.92 (2H, d, J=11, NCH$_2$CH$_A$H$_B$), 2.08 (2H, t, J=11, NCH$_A$H$_B$), 2.53 (2H, t, J=7.1, PhCH$_2$), 2.56–2.64 (1H, m, CHCN), 2.75 (2H, t, J=7.1, PhCH$_2$CH$_2$), 3.00 (2H, d, J=11, NCH$_A$H$_B$), 6.59 (1H, s, pyrazole H-4), 7.1–7.3 (6H, m, Ph and pyridine-H), 7.76–7.82 (1H, m, pyridine-H), 7.84–7.93 (1H, m, pyridine-H), 8.52–8.60 (1H, m, pyridine H-6), 12.75 (1H, s, NH); m/z (CI$^+$, NH$_3$) 333 (M$^+$+H).

EXAMPLE 43

3-(4-(1-Benzyl-4-methylpiperidinyl))-5-(4-chlorophenyl)pyrazole dihydrobromide White granules, m.p. 222°–225° C. (from EtOH/DMF) (Found: C, 50.2; H, 5.0; N, 8.1. $C_{22}H_{24}N_3Cl$ .2HBr requires C, 50.1; H, 5.0; N, 8.0%); $\delta_H$ (360 MHz, d$_6$-DMSO +CF$_3$CO$_2$D) 2.5:1 mixture of invertomers at the protonated nitrogen was observed. Peaks for major isomer: 1.24 (3H, s, CH$_3$), 1.86–2.04 (2H, m, 2×NCH$_2$CH$_A$H$_B$), 2.43 (2H, d, J=14, 2×NCH$_2$CH$_A$H$_B$), 2.86–2.99 (2H, m, 2×NCH$_A$H$_B$C$_2$), 3.24–3.36 (2H, m, 2×NCH$_A$H$_B$C$_2$), 4.28 (2H, d, J=5, NCH$_2$Ph), 6.79 (1H, s, 1 of ArH), 7.44–7.52 (7H, m, 7 of ArH), 7.82 (2H, d, J=9, 2 of ArH) and 9.5 (1H, broad s, NH). Peaks visible for minor isomer: 2.14–2.23 (2H, m, 2×NCH$_2$CH$_A$H$_B$), 4.45 (2H, d, J=5, NCH$_2$Ph), 6.65 (1H, s, 1 of ArH) and 7.79 (2H, d, J=9, 2 of ArH); m/z (CI$^+$; NH$_3$) 366 (M$^+$+H).

EXAMPLE 44

3-(4-(1-(Indol-3-ylmethyl)piperidinyl))-5-(4-chlorophenyl)pyrazole

White prisma, m.p. 128°–132° C. (from EtOH/DMF) (Found: C, 68.9; H, 6.8; N, 12.9. $C_{23}H_{23}N_4Cl.C_2H_5OH$ requires C, 68.7; N, 6.7; N, 12.8%); $\delta_H$ (360 MHz, CDCl$_3$) 1.19 (3H, t, J=7, CH$_3$CH$_2$OH), 1.79 (2H, broad q, J=11, 2×NCH$_2$CH$_A$H$_B$), 1.96 (2H, broad d, J=11, 2×NCH$_2$CH$_A$H$_B$), 2.16 (2H, broad t, J=11, 2×NCH$_A$H$_B$C$_2$), 2.66 (1H, tt, J=11 and 4, NCH$_2$CH$_2$CH), 3.07 (2H, broad d, J=11, 2×NCH$_A$H$_B$C$_2$), 3.50 (1H, broad s, CH$_3$CH$_2$OH), 3.63 (2H, q, J=7, CH$_3$CH$_2$OH), 3.78,(2H, s, NCH$_2$Ar), 6.29 (1H, s, 1 of ArH). 7.04–7.16 (3H, m, 3 of ArH), 7.30–7.33 (2H, m, 2 of ArH), 7.38 (1H, d, J=8, 1 of ArH), 7.69–7.71 (3H, m, 3 of ArH, 9.99 (1H, broad s, NH) and 12.15 (1H, broad s, NH); m/z (CI$^-$; NH$_3$) 390 (M$^-$; 3%), 296 (12) and 178 (100).

EXAMPLE 45

3-(4-(1-(2-Phenylethyl)piperidinyl))-4-methyl-5-(4-chlorophenyl)pyrazole

White needles, m.p. 181°–183° C. (from EtOH/H$_2$O) (Found: C, 71.4; H, 7.0; N, 10.8. $C_{23}H_{26}N_3Cl.0.375$ H$_2$O requires C, 71.4; H, 7.0; N, 10.9%); $\delta_H$ (360 MHz, CDCl$_3$) 1.92–2.02 (4H, m, 2×NCH$_2$CH$_2$), 2.14 (3H, s, CH$_3$) 2.15–2.18 (2H, m, 2×NCH$_A$H$_B$C$_2$), 2.65–2.77 (3H, m, NCH$_2$CH$_2$CH and NCH$_2$CH$_2$Ph), 2.83–2.87 (2H, m, NCH$_2$CH$_2$Ph), 3.16 (2H, broad d, J=12, 2×NCH$_A$H$_B$C$_2$), 7.18–7.22 (3H, m, 3 of ArH), 7.25–7.31 (2H, m, 2 of ArH), 7.33–7.40 (2H, m, 2 of ArH) and 7.50 (2H, d, J=8, 2 of ArH); m/z (CI$^+$; NH$_3$) 380 (M$^+$+H; 100%).

EXAMPLE 46

3-(3-(1-Benzylpiperidinyl))-5-(4-chlorophenyl)pyrazole dihydrobromide

White cubes, m.p. 215°–218° C. (from EtOH/EtOAc) (Found: C, 48.7; H, 4.9; N, 7.9. $C_{21}H_{22}N_3Cl.2HBr.0.25$ (H$_2$O) requires C, 48.8; H, 4.6; N, 8.1%); $\delta_H$ (360 MHz, CDCl$_3$+CD$_3$OD) 2.01–2.26 (4H, m, NCH$_2$CH$_2$CH$_2$), 3.28–3.37 (1H, m, NCH$_A$H$_B$C$_2$), 4.47 (1H, broad d, J=11, NCH$_A$H$_B$C$_2$), 3.57–3.64 (2H, m, NCH$_2$CH), 3.84–3.90 (1H, m, NCH$_2$CH), 4.43–4.49 (2H, m, NCH$_2$Ph, partly obscured by solvent peaks), 7.05 (1H, s, 1 of ArH), 7.44–7.52 (5H, m, 5 of ArH) and 7.69–7.40 (4H, m, 4 of ArH); m/z (CI$^+$; NH$_3$) 352 (MH$^+$; 85%), 238 (30) and 128 (100).

EXAMPLE 47

3-(3-(1-Benzylpyrrolidinyl))-5-(4-chlorophenyl)-pyrazole dihydrochloride

White cubes, m.p. 155°–159° C. (from EtOH/EtOAc) (Found: C, 58.6; H, 5.4; N, 10.2 $C_{20}H_{20}N_3Cl.2HCl$ requires C, 58.5; H, 5.4; N, 10.2%); $\delta_H$ (360 MHz, d$_6$-DMSO) 2.16–2.38 (1H, broad m, NCH$_2$CH$_A$H$_B$), 2.45–2.64 (1H, broad m, NCH$_2$CH$_A$H$_B$), 3.30–3.60 (3H, broad m, NCH$_2$ and NCH$_2$CH), 3.64–3.90 (2H, broad m, NCH$_2$), 4.42 (2H, s, NCH$_2$Ph), 6.76 (1H, s, 1 of ArH), 7.36–7.51 (5H, m, 5 of ArH), 7.50–7.53 (2H, m, 2 of ArH) and 7.63 (2H, d, J=9, 2 of ArH); m/z (CI$^+$; NH$_3$) 338 (MH$^+$; 100%).

EXAMPLES 48 & 49

3-(4-(1-Benzyl)piperidinyl)-5-(2-thienyl)isoxazole and 5-(4-(1-Benzyl)piperidinyl)-3-(2-thienyl)isoxazole Two isoxazole isomers of undetermined regiochemistry.
ISOMER A
Yellow crystals, m.p. 95°–97° C. (from ethanol/water) (Found: C, 70.04; H, 6.16; N, 8.52. C$_{19}$H$_{20}$N$_2$OS requires C, 70.34; H, 6.21; N, 8.63%); $\delta_H$ (360 MHz, CDCl$_3$) 1.92–1.98 (4H, m, CH$_A$H$_B$CH and CH$_A$H$_B$CH), 2.2–2.25 (2H, m, CH$_A$H$_B$N), 2.83 (1H, m, CH$_2$CHCH$_2$), 3.03 (2H, d, J=11.2, CH$_A$H$_B$N), 3.61 (2H, s, ArCH$_2$), 6.28 (1H, s, CCHC), 7.09–7.14 (1H, m, CArH), 7.26–7.48 (7H, m, CH$_2$ArH and CArH); m/z (CI$^+$, NH$_3$) 325 (M$^+$+H).
ISOMER B
Yellow crystals, m.p. 81°–83° C. (from ethanol/water) (Found: C, 68.10; H, 6.21; N, 8.91. C$_{19}$H$_2$N$_2$OS.0.5H$_2$O requires C, 68.43; H, 6.35; N, 8.40%); $\delta_H$ (360 MHz, CDCl$_3$) 1.82–1.85 (2H, m, CH$_A$H$_B$CH), 2.06 (2H, br d, J=12.5, CH$_A$H$_B$CH), 2.14 (2H, t, J=11, CH$_A$H$_B$N), 2.75–2.85 (1H, m, CH$_2$CHCH$_2$), 2.97 (2H, d, J=11, CH$_A$H$_B$N), 3.55 (2H, s, ArCH$_2$), 6.20 (1H, s, CCHC), 7.09–7.11 (1H, m, CArH), 7.26–7.43 (7H, m, CH$_2$ArH and CArH); m/z (CI$^+$, NH$_3$) 325 (M$^+$+H).

EXAMPLE 50

3-(1-(2-Phenylethyl)-4-piperidinyl)-5-(4-chlorophenyl)isoxazole

White needles, m.p. 118°–120° C. (from ethanol/water) (Found: C, 69.63; H, 6.48; N, 7.38. C$_{22}$H$_{23}$N$_2$OCl.0.7H$_2$O requires C, 69.73; H, 6.40; N, 7.34%); $\delta_H$ (360 MHz, d$_6$-DMSO) 1.7–1.8 (2H, m, NCH$_2$CH$_A$H$_B$), 1.92 (2H, d, J=13, NCH$_2$CH$_A$H$_B$), 2.1–2.2 (2H, m, NCH$_A$H$_B$), 2.5–2.6 (3H, m, CH and CH$_2$), 2.7–2.8 (4H, m, CH$_2$'s), 3.0–3.1 (2H, m, CH$_2$), 7.08 (1H, s, isoxazole-H), 7.2–7.4 (5H, m, Ph), 7.60 (2H, d, J=6.8, ArH o to Cl), 7.85 (2H, d, J=6.8, ArH m to Cl); m/z (CI$^+$, NH$_3$) 367 (M$^+$+H).

EXAMPLE 51

3-(1-Benzyl-4-piperidinyl)-5-(4-chlorophenyl)isoxazole

White plates, m.p. 112°–114° C. (from ethanol) (Found: C, 71.65; H, 6.09; N, 8.01. C$_{21}$H$_{21}$N$_2$OCl requires C, 71.48; H, 6.00; N, 7.94%); $\delta_H$ (360 MHz, d$_6$-DMSO) 1.7–1.8 (2H, m, NCH$_2$CH$_A$H$_B$), 1.89 (2H, d, J=11, NCH$_2$CH$_A$H$_B$), 2.08 (2H, t, J=10, NCH$_A$H$_B$), 2.75 (1H, tt, J=4 and 11, CH$_2$CH), 2.67 (2H, d, J=10, NCH$_A$H$_B$), 3.49 (2H, s, ArCH$_2$), 7.06 (1H, s, isoxazole-H), 7.2–7.3 (5H, m, Ph), 7.60 (2H, d, J=7, ArH o to Cl), 7.84 (2H, d, J=7, ArH m to Cl); m/z (CI$^+$, NH$_3$) 353 (M$^+$+H).

EXAMPLE 52

3-(4-Chlorophenyl)-4-methyl-5-(4-(1-(2-phenylethyl) piperidinyl))isoxazole

White needles, m.p. 130°–131° C. (from EtOH/H$_2$O) (Found: C, 72.25; H, 6.9; N, 7.3. C$_{23}$H$_{25}$N$_2$ClO requires C, 72.5; H, 6.6; N, 7.4%); $\delta_H$ (360 MHz, CDCl$_3$) 1.40–1.75 (2H, broad m, 2×NCH$_2$CH$_A$H$_B$), 1.90–2.40 (4H, broad m, 2×NCH$_2$CH$_A$H$_B$ and 2×NCH$_A$H$_B$C$_2$), 2.09 (3H, s, CH$_3$), 2.70–2.80 (2H, broad m, NCH$_2$CH$_2$Ph), 2.70–2.80 (2H, m, NCH$_2$CH$_2$Ph), 2.84–2.98 (3H, broad m, NCH$_2$CH$_2$Ph and NCH$_2$CH$_2$CH), 3.18 (2H, broad d, J=12, 2×NCH$_A$H$_B$C$_2$), 7.20–7.33 (5H, m, Ph), 7.43–7.46 (2H, m, 2 of ArH) and 7.57–7.59 (2H, m, 2 of ArH); m/z (CI$^+$; NH$_3$) 381 (M$^+$+H; 100%).

EXAMPLE 53

3-(4-(1-(2-Phenylethyl)piperidinyl))-4-methyl-5-(4-chlorophenyl)isoxazole

White plates, m.p. 138°–140° C. (from EtOH/H$_2$O) (Found: C, 72.5; H, 6.7; N, 7.6. C$_{23}$H$_{25}$N$_2$ClO requires C, 72.5; H, 6.6; N,7.4%); $\delta_H$ (360 MHz, CDCl$_3$) 2.00–2.10 (4H, broad m, 2×NCH$_2$CH$_2$), 2.19 (3H, s, CH$_3$), 2.12–2.32 (2H, broad m, 2×NCH$_A$H$_B$C$_2$), 2.65–2.75 (3H, m, NCH$_2$CH$_2$CH and NCH$_2$CH$_2$Ph), 2.85–2.89 (2H, m, NCH$_2$CH$_2$Ph), 3.15 (2H, broad d, J=12, 2×NCH$_A$H$_B$CH$_2$), 7.18–7.32 (5H, m, Ph), 7.44–7.47 (2H, m, 2 of ArH) and 7.57–7.64 (2H, m, 2 of ArH); m/z (CI$^+$; NH$_3$) 381 (M$^+$+H; 10%), 215 (15), 134 (20) and 76 (100). The isoxazole regiochemistry was proved by x-ray.

EXAMPLE 54

3-(4-(1-Benzylpiperidinyl))-4-ethyl-5-(4-chlorophenyl)pyrazole

Colourless cubes, m.p. 170°–172° C. (from EtOH) (Found: C, 72.9; H, 6.9; N, 11.1. C$_{23}$H$_{26}$N$_3$Cl requires C, 72.7; H, 6.9; N, 11.1%); $\delta_H$ (360 MHz, CDCl$_3$) 1.09 (3H, t, J=7.5, CH$_2$CH$_3$), 1.67–1.89 (4H, m, 2×NCH$_2$CH$_2$), 2.07–2.18 (2H, m, 2×NCH$_A$H$_B$C$_2$), 2.56 (2H, q, J=7.5, CH$_2$CH$_3$), 2.69 (1H, tt, J=8 and 8, NCH$_2$CH$_2$CH), 3.03 (2H, broad d, J=12, 2×NCH$_A$CH$_B$), 3.57 (2H, s, NCH$_2$Ph), 7.26–7.39 (7H, m, 7 of ArH) and 7.50 (2H, d, J=8, 2 of ArH); m/z (CI$^+$; NH$_3$) 380 (M$^+$+H; 100%).

EXAMPLE 55

2,4-Dimethyl-3-(4-(1-benzylpiperidinyl))-5-(4-chlorophenyl) pyrazole oxalate

White granules, m.p. 215°–217° C. (from EtOH) (Found: C, 63.7; H, 6.1; N, 8.7. C$_{23}$H$_{26}$N$_3$Cl.(CO$_2$H)$_2$.0.1(H$_2$O) requires C, 63.65; H, 6.0; N, 8.9%); $\delta_H$ (360 MHz, d$_6$-DMSO) 1.86 (2H, broad d, J=13, 2×NCH$_2$CH$_A$H$_B$), 2.08–2.18 (2H, m, 2×NCH$_2$CH$_A$H$_B$), 2.15 (3H, s, CH$_3$), 2.77 (2H, broad t, J=12, 2×NCH$_A$H$_B$C$_2$), 3.03 (1H, broad t, J=12, NCH$_2$CH$_2$CH), 3.31 (2H, broad d, J=11, 2×NCH$_A$H$_B$C$_2$), 3.82 (3H, s, NCH$_3$), 4.10 (2H, s, NCH$_2$Ph), 7.43–7.48 (7H, m, 7 of ArH) and 5.54 (2H, d, J=8.5, 2 of ArH); m/z (CI$^+$; NH$_3$) 380 (M$^+$+H; 100%). The pyrazole regiochemastry was proved by nOe experiments.

EXAMPLE 56

1,4-Dimethyl-3-(4-(1-benzylpiperidinyl))-5-(4-chlorophenyl) pyrazole oxalate

White granules, m.p. 165°–166° C. (from EtOH) (Found: C, 62.2; H, 5.9; N, 8.5. C$_{23}$H$_{26}$H$_3$Cl.(CO$_2$H)$_2$.0.75(H$_2$O) requires C, 62.1; H, 6.15; N, 8.7%); $\delta_H$ (360 MHz, d$_6$-DMSO) 1.90 (3H, s, CH$_3$), 1.92–2.02 (4H, broad m, 2×NCH$_2$CH$_2$), 2.76–2.96 (3H, broad m, NCH$_2$CH$_2$CH and 2×NCH$_A$H$_B$C$_2$), 3.31 (2H, broad d, J=12, 2×NCH$_A$H$_B$CH$_2$), 3.63 (3H, s, NCH$_3$), 4.15 (2H, s, NCH$_2$Ph), 7.40–7.55 (7H, m, 7 of ArH) and 7.56 (2H, d, J=6.5, 2 of ArH); m/z (CI$^+$; NH$_3$) 380 (M$^+$+H; 100%). The pyrazole regiochemistry was proved by nOe experiments.

EXAMPLE 57

3-(4-(1-(2-Phenylethyl)piperidinyl))-4-methoxy-5-phenylpyrazole

Colourless needles, m.p. 153°–154° C. (from EtOAc) (Found: C, 76.05; H, 7.4; N, 11.6. $C_{23}H_{27}N_3O.0.1(H_2O)$ requires C, 76.0; H, 7.6; N, 11.6%); $\delta_H$ (360 MHz, CDCl$_3$) 2.02–2.18 (4H, broad m, 2×NCH$_2$CH$_2$), 2.24–2.44 (2H, broad m, 2×NCH$_A$H$_B$C$_2$), 2.78–3.00 (5H, m, NCH$_2$CH$_2$CH and NCH$_2$CH$_2$Ph), 3.24 (2H, broad d, J=12, 2×NCH$_A$H$_B$CH$_2$), 3.68 (3H, s, OCH$_3$), 7.19–7.55 (6H, m, 6 of ArH), 7.42 (2H, t, J=7, 2 of ArH) and 7.79 (2H, d, J=7.5, 2 of ArH); m/z (CI$^+$; NH$_3$) 362 (M$^+$+H; 100%).

EXAMPLE 58

E-3-(4-(1-(3-Phenylprop-2-enyl)piperidinyl))-5-(4-chlorophenyl)pyrazole

Yellow diamonds, m.p. 174°–175° C. (from ethanol) (Found: C, 72.67; H, 6.42; N, 10.98. $C_{23}H_{24}N_3Cl.1.0.1$ (H$_2$O) requires C, 72.75; H, 6.42; N, 11.07%); $\delta_H$ (360 MHz, d$_6$-DMSO) 1.6–1.7 (2H, m, CH$_A$H$_B$CHC), 1.92 (2H, d, J=10.8, CH$_A$H$_B$CHC), 2.06 (2H, t, J=10, CH$_A$H$_B$N), 2.60–2.70 (1H, m, CH$_2$CHC), 2.96 (2H, brd, J=10, CH$_A$H$_B$N), 3.12 (2H, d, J=6.4, CHCH$_2$N), 6.28–6.36 (1H, m, CHCH$_2$N), 6.52–6.56 (2H, m, CCHC and ArCHCH), 7.23 (1H, t, J=7.4, CHArH), 7.33 (2H, t, J=7.4, CHArH), 7.44–7.46 (4H, m, CHArH and CArH), 7.78 (2H, d, J=7.2, CArH), 12.69 (1H, brs, NH); m/z (CI$^+$, NH$_3$) 378 (MH$^+$; 100%).

EXAMPLE 59

3-(4-(1-(1-Naphthylmethyl)piperidinyl))-5-(4-chlorophenyl)pyrazole

Fine white crystals, m.p. 174°–177° C. (from ethyl acetate) (Found: C, 75.27; H, 6.18; N, 10.14. $C_{25}H_{24}N_3Cl$ requires C, 74.71; H, 6.02; N, 10.45%); $\delta_H$ (360 MHz, d$_6$-DMSO) 1.6–1.7 (2H, m, CH$_A$H$_B$CH), 1.88 (2H, br d, J=12.2, CH$_A$H$_B$CH), 2.15 (2H, t, J=11.7, CH$_A$H$_B$N), 2.68 (1H, m, CH$_2$CH), 2.95 (2H, br d, J=11.7, CH$_A$H$_B$N), 3.89 (2H, s, CCH$_2$N), 6.50 (1H, brs, CCHC), 7.43–7.56 (6H, m, CH$_2$ArH and CArH), 7.76 (2H, br d, J=7.6, CArH), 7.83–7.86 (1H, m, CH$_2$ArH), 7.91–7.93 (1H, m, CH$_2$ArH), 8.30 (1H, d, J=7.8, CH$_2$ArH); m/z (CI$^+$, NH$_3$) 402 (M$^+$+H).

EXAMPLE 60

3-(4-(1-(2-Furanylmethyl)-piperidinyl))-4-methyl-5-phenylpyrazole

White needles, m.p. 137°–138° C. (from ethyl acetate) (Found: C, 75.07; H, 7.08; N, 13.11. $C_{20}H_{23}N_3O$ requires C, 74.74; H, 7.21; N, 13.07%); $\delta_H$ (360 MHz, d$_6$-DMSO) 1.7–1.8 (4H, m, CH$_A$H$_B$CH and CH$_A$H$_B$CH), 2.04–2.08 (2H, m, CH$_A$H$_B$N), 2.08 (3H, s, CH$_3$), 2.5–2.6 (1H, m, CH$_2$CHCH$_2$), 2.9 (2H, br d, J=11.4, CH$_A$H$_B$N), 3.52 (2H, s, ArCH$_2$), 6.29 (1H, d, J=3.0, ArH), 6.40–6.41 (1H, m, ArH), 7.31–7.59 (6H, m, ArH), 12.44 (1H, br s, NH); m/z (CI$^+$, NH$_3$) 322 (M$^+$+H).

EXAMPLE 61

3-(4-(1-(2-(4-Methoxyphenyl)ethyl)piperidinyl))-4-methyl-5-phenylpyrazole

White needles, m.p. 176°–178° C. (from ethyl acetate) (Found: C, 76.66; H, 7.74; N, 11.18. $C_{24}H_{29}N_3O$ requires C, 76.76; H, 7.78; N, 11.19%); $\delta_H$ (360 MHz, d$_6$-DMSO) 1.7–1.8 (4H, m, CH$_A$H$_B$CH and CH$_A$H$_B$CH), 2.02–2.08 (2H, m, CH$_A$H$_B$N), 2.08 (3H, s, CH$_3$), 2.50 (2H, t, J=7.0, ArCH$_2$CH$_2$), 2.60–2.64 (1H, m, CH$_2$CHCH$_2$), 2.69 (2H, t, J=7.0, ArCH$_2$), 3.03 (2H, br d, J=11.2, CH$_A$H$_B$N), 3.72 (3H, s, CH$_3$O), 6.65 (2H, d, J=8.7, MeOArH), 7.15 (2H, d, J=8.7, MeOArH), 7.25–7.3 (1H, m, CArH p to C), 7.4–7.5 (2H, m, CArH), 7.5–7.6 (2H, m, CArH), 12.47 (1H, br s, NH); m/z (CI$^+$, NH$_3$) 376 (M$^+$+H).

EXAMPLE 62

3-(4-(1-(2-Oxo-2-phenylethyl)piperidinyl))-4-methyl-5-phenylpyrazole

Pale yellow crystals, m.p. 176°–178° C. (from ethyl acetate) (Found: C, 76.85; H, 6.91; N, 11.76. $C_{23}H_{25}N_3O$ requires C, 76.85; H, 7.01; N, 11.69%) $\delta_H$ (360 MHz, d$_6$-DMSO) 1.72–1.84 (4H, m, CH$_A$H$_B$CH and CH$_A$H$_B$CH), 2.10 (3H, s, CH$_3$), 2.26 (2H, t, J=11.2, CH$_A$H$_B$N), 2.6–2.65 (1H, m, CH$_2$CHCH$_2$), 3.01 (2H, br d, J=11.2, CH$_A$H$_B$N), 3.86 (2H, s, COCH$_2$), 7.32 (1H, t, J=7.2, ArH), 7.42 (2H, t, J=7.4, ArH), 7.51–7.58 (4H, m, ArH), 7.64 (1H, t, J=7.4, ArH), 8.02 (2H, d, J=8.7, ArH), 12.48 (1H, br s, NH), m/z (CI$^+$, NH$_3$) 360 (M$^+$+H).

EXAMPLE 63

3-(4-(1-(2-(3-Pyridyl)ethyl)piperidinyl))-4-methyl-5-phenylpyrazole

White needles, m.p. 188°–190° C. (from ethanol) (Found: C, 75.66; H, 7.33; N, 15.89. $C_{22}H_{26}N_4.0.2(H_2O)$ requires C, 75.48; H, 7.60; N, 16.00%); $\delta_H$ (360 MHz, 353K, d$_6$-DMSO) 1.9–2.0 (4H, m, CH$_A$H$_B$CH and CH$_A$H$_B$CH), 2.11 (3H, s, CH$_3$), 2.6–2.7 (1H, m, CH$_2$CHCH$_2$), 2.80–3.04 (6H, m, CH$_A$H$_B$N and CH$_2$CH$_2$Ar), 3.29 (2H, br s, CH$_A$H$_B$N), 7.29–7.33 (2H, m, ArH), 7.42 (2H, t, J=7.4, ArH), 7.55 (2H, d, J=7.4, ArH), 7.68 (1H, d, J=7.6, ArH), 8.43 (1H, d, J=7.2, CH$_2$ArH p to CH$_2$), 8.50 (1H, s, CH$_2$ArH o to CH$_2$ and o to N), 12.54 (1H, br s, NH); m/z (CI$^+$, NH$_3$) 347 (M$^+$+H).

EXAMPLE 64

3-(4-(1-(2-(1,2,3,4-Tetrahydronaphthyl))piperidinyl))-5-(4-chlorophenyl) pyrazole White needles, m.p. 171°–173° C. (from ethyl acetate); $\delta_H$ (360 MHz, d$_6$-DMSO) 1.60–1.69 (3H, m, CHCH$_A$H$_B$CH$_2$ and ArCH$_2$CH$_A$H$_B$), 1.92–1.99 (3H, m, CHCH$_A$H$_B$CH$_2$ and ArCH$_2$CH$_A$H$_B$), 2.29–2.39 (2H, m, CH$_2$), 2.64–2.86 (6H, m, CH$_2$), 2.96–3.04 (2H, m, CH$_2$), 6.51 (1H, s, CCHC), 7.0–7.1 (4H, m, ArHCH$_2$), 8.43 (2H, d, J=7.6, ArH), 7.78 (2H, d, J=7.6, ArH), 12.67 (1H, s, NH); m/z (CI$^+$, NH$_3$) 392 (M$^+$+H).

EXAMPLE 65

3-(4-(1-(2-Phenylethyl)piperidinyl))-4-chloro-5-(4-chlorophenyl)pyrazole

A solution of tert-butyl hypochlorite (131 mg, 1.2 mmol) in dichloromethane (4 ml) was added slowly to a solution of 3-(4-(1-(2-phenylethyl)piperidinyl))-5-(4-chlorophenyl) pyrazole (440 mg, 1.2 mmol) and the resulting pale yellow solution stirred for 3 h, under N$_2$. Solvents were removed in vacuo to give pale yellow crystals. Recrystallisation of the product from ethanol yielded the desired product (310 mg, 64%) as off-white crystals, m.p. 160°–162° C. (from ethanol) (Found: C, 64.11; H, 5.94; N, 10.06. $C_{22}H_{23}N_3Cl_2 \cdot 0.6(H_2O)$ requires C, 64.27; H, 5.93; N, 10.22%); $\delta_H$ (360 MHz, $d_6$-DMSO) 1.75–1.85 (4H, m, CHCH$_2$), 2.03–2.10 (2H, m, NCH$_A$H$_B$C$_2$CH), 2.55 (2H, t, J=7.2, NCH$_2$), 2.7–2.75 (1H, m, CHCH$_2$), 2.76 (2H, t, J=7.2, ArCH$_2$), 3.05 (2H, d, J=11.3, NCH$_A$H$_B$C$_2$CH), 7.16–7.30 (5H, m, CH$_2$ArH), 7.54 (2H, d, J=8.3, ArH), 7.82 (2H, d, J=8.3, ArH), 13.20 (1H, s, NH); m/z (CI$^+$, NH$_3$) 400 (M+H).

We claim:

1. A compound of formula I, or a pharmaceutically acceptable salt thereof or a prodrug thereof:

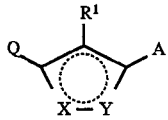  (I)

wherein the broken circle represents two non-adjacent double bonds to form a pyrazole, isoxazole or isothiazole ring;

one of X and Y represents nitrogen, and the other of X and Y represents oxygen, sulphur or N—R$^2$;

Q represents a ring of formula Qa to Qe

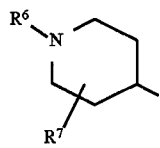  (Qa)

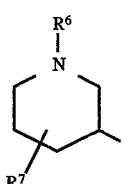  (Qb)

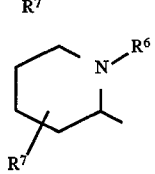  (Qc)

R$^1$ represents hydrogen, halogen, C$_{1-6}$ alkyl, hydroxy or C$_{1-6}$ alkoxy;

R$^2$ represents hydrogen or C$_{1-6}$ alkyl;

A represents a group of formula (i), (ii) or (iii):

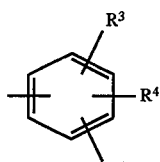  (i)

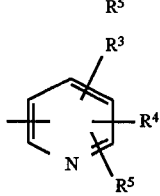  (ii)

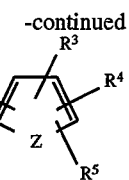  (iii)

in which Z represents oxygen, sulphur or NH;

R$^3$, R$^4$ and R$^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$;

R$^a$ and R$^b$ independently represent hydrogen, hydrocarbon or a heterocyclic group;

R$^6$ represents C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$)alkyl, aryl (C$_{2-6}$)alkenyl, aryl(C$_{2-6}$)alkynyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted; and R$^7$ represents hydrogen, C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$)alkyl, aryl(C$_{2-6}$)alkenyl, aryl(C$_{2-6}$) alkynyl, C$_{3-7}$ heterocycloalkyl, C$_{3-7}$ heterocycloalkyl (C$_{1-6}$)alkyl, heteroaryl or heteroaryl(C$_{1-6}$)alkyl, any of which groups may be optionally substituted.

2. A compound as claimed in claim 1 represented by formula IA, or a pharmaceutically acceptable salt prodrug thereof:

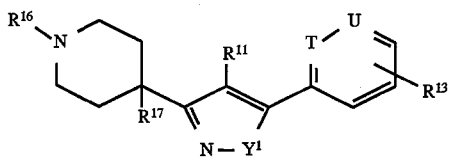  (IA)

wherein

Y$^1$ represents oxygen, sulphur or N—R$^{12}$;

one of T and U represents CH and the other represents CH or N;

R$^{11}$ represents hydrogen, halogen, C$_{1-6}$ alkyl or C$_{1-6}$ alkoxy;

R$^{12}$ represents hydrogen or C$_{1-6}$ alkyl;

R$^{13}$ represents hydrogen, halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkyl carbonyl;

R$^{16}$ represents C$_{2-6}$ alkenyl, C$_{3-7}$ cycloalkyl(C$_{1-6}$)alkyl, aryl, aryl(C$_{1-6}$)alkyl, aryl(C$_{2-6}$)alkenyl or heteroaryl (C$_{1-6}$)alkyl, any of which groups may be optionally substituted; and R$^{17}$ represents hydrogen or methyl.

3. A compound as claimed in claim 1 represented by formula IB, or a pharmaceutically acceptable salt or a prodrug thereof:

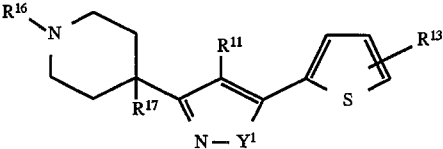  (IB)

4. A compound as claimed in claim 1 represented by formula IC, or a pharmaceutically acceptable salt or a prodrug thereof:

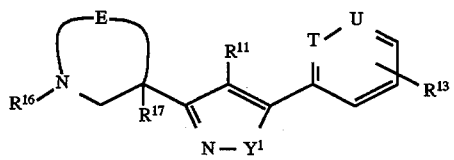

wherein

E represents a linking group of formula —$(CH_2)_3$—; and wherein $Y^1$ represents oxygen, sulphur or N—$R^{12}$; one of T and U represents CH and the other represents CH or N; $R^{11}$ represents hydrogen, halogen, $C_{1-6}$alkyl or $C_{1-6}$alkoxy; $R^{12}$ represents hydrogen or $C_{1-6}$alkyl; $R^{13}$ represents hydrogen, halogen, trifluromethyl, cycano, nitro, amino, $C_{1-6}$alkylamino, di($C_{1-6}$)alkylamino, $C_{1-6}$alkyl, $C_{1-6}$alkoxy, aryl($C_{1-6}$)alkoxy or $C_{2-6}$alkylcarbonyl; $R^{16}$ represents $C_{2-6}$alkenyl, $C_{3-7}$cycloalkyl($C_{1-6}$)alkyl, aryl, aryl($C_{1-6}$)alkyl, aryl ($C_{2-6}$)alkenyl or heteroaryl($C_{1-6}$)alkyl, any of which groups may be optionally substituted; and $R^{17}$ represents hydrogen or methyl.

5. A compound selected from:
3-[1-(4-chlorobenzyl)piperidin-4-yl]-5-(4-chlorophenyl) pyrazole;
3-(1-benzylpiperidin-4-yl)-5-(4-chlorophenyl)pyrazole;
5-(4-chlorophenyl)-3-[1-(4-methylbenzyl)piperidin-4-yl] pyrazole;
5-(4-chlorophenyl)-3-[1-(4-methoxybenzyl)piperidin-4-yl] pyrazole;
5-(4-chlorophenyl)-3-[1-(prop-2-en-1-yl)piperidin-4-yl] pyrazole;
5-(4-chlorophenyl)-3-[1-(4-nitrobenzyl)piperidin-4-yl] pyrazole;
3-[1-(4-chlorobenzyl)piperidin-4-yl]-5-phenylpyrazole;
3-[1-(4-chlorobenzyl)piperidin-4-yl]-5-(2-thienyl)- pyrazole;
3-[1-(4-chlorobenzyl)piperidin-4-yl]-5-(4-isopropylphenyl) pyrazole;
3-[1-(4-chlorobenzyl)piperidin-4-yl]-5-(4-methoxyphenyl) pyrazole;
5-(4-chlorophenyl)-3-(1-cyclohexylmethylpiperidin-4-yl)- pyrazole;
5-(4-chlorophenyl)-3-[1-(2-phenylethyl)piperidin-4-yl]- pyrazole;
5-(4-chlorophenyl)-3-[1-(3,4-dichlorobenzyl)piperidin-4-yl]pyrazole;
3-[1-(4-chlorobenzyl)piperidin-4-yl]-5-(3-chlorophenyl) pyrazole;
3-[1-(3-chlorobenzyl)piperidin-4-yl]-5-(4-chlorophenyl) pyrazole;
5-[1-(4-chlorobenzyl)piperidin-4-yl]-3-(4-chlorophenyl)-1-methylpyrazole;
3-[1-(4-chlorobenzyl)piperidin-4-yl]-5-(4-chlorophenyl)-1-methylpyrazole;
3-[1-(4-chlorobenzyl)piperidin-4-yl]-5-(2-chlorophenyl) pyrazole;
3-(1-benzylpiperidin-4-yl)-5-phenylpyrazole;
3-[1-(4-chlorobenzyl)piperidin-4-yl]-5-(4-chlorophenyl) isoxazole;
5-[1-(4-chlorobenzyl)piperidin-4-yl]-3-(4-chlorophenyl) isoxazole;
3-[1-(4-chlorobenzyl)piperidin-4-yl]-5-(2-methoxyphenyl) pyrazole;
5-(4-chlorophenyl)-3-[1-(2-methylbenzyl)piperidin-4-yl]- pyrazole;
5-(4-chlorophenyl)-3-[1-(3-nitrobenzyl)piperidin-4-yl]- pyrazole;
5-(4-chlorophenyl)-3-[1-(3-methylbenzyl)piperidin-4-yl]- pyrazole;
5-(4-chlorophenyl)-3-[1-(2-nitrobenzyl)piperidin-4-yl]- pyrazole;
3-[1-(4-chlorobenzyl)piperidin-4-yl]-4-methyl-5-phenylpyrazole;
3-[1-(2-chlorobenzyl)piperidin-4-yl]-5-(4-chlorophenyl) pyrazole;
5-(4-chlorophenyl)-3-(1-cyclopropylmethylpiperidin-4-yl) pyrazole;
3-(1-benzylpiperidin-4-yl)-5-(4-chlorophenyl)-4-methylpyrazole;
5-(4-chlorophenyl)-3-[1-(2-naphthylmethyl)piperidin-4-yl] pyrazole;
5-(4-chlorophenyl)-3-[1-(3-phenylpropyl)piperidin-4-yl] pyrazole;
5-(4-chlorophenyl)-3-[1-(3-methoxybenzyl)piperidin-4-yl] pyrazole;
3-[1-(2-phenylethyl)piperidin-4-yl]-5-(2-pyridyl)pyrazole;
3-(1-benzyl-4-methylpiperidin-4-yl)-5-(4-chlorophenyl) pyrazole;
5-(4-chlorophenyl)-3-[1-(indol-3-ylmethyl)piperidin-4-yl] pyrazole;
5-(4-chlorophenyl)-4-methyl-3-[1-(2-phenylethyl) piperidin-4-yl]pyrazole;
3-(1-benzylpiperidin-3-yl)-5-(4-chlorophenyl)pyrazole;
3-(1-benzylpiperidin-4-yl)-5-(2-thienyl)isoxazole;
5-(1-benzylpiperidin-4-yl)-3-(2-thienyl)isoxazole;
5-(4-chlorophenyl)-3-[1-(2-phenylethyl)piperidin-4-yl] isoxazole;
3-(1-benzylpiperidin-4-yl)-5-(4-chlorophenyl)isoxazole;
3-(4-chlorophenyl)-4-methyl-5-[1-(2-phenylethyl) piperidin-4-yl]isoxazole;
5-(4-chlorophenyl)-4-methyl-3-[1-(2-phenylethyl) piperidin-4-yl]isoxazole;
3-(1-benzylpiperidin-4-yl)-5-(4-chlorophenyl)-4-ethylpyrazole;
5-(1-benzylpiperidin-4-yl)-3-(4-chlorophenyl)-1,4-dimethylpyrazole;
3-(1-benzylpiperidin-4-yl)-5-(4-chlorophenyl)-1,4-dimethylpyrazole;
4-methoxy-5-phenyl-3-[1-(2-phenylethyl)piperidin-4-yl] pyrazole;
5-(4-chlorophenyl)-3-[1-(3-E-phenylprop-2-en-1-yl) piperidin-4-yl]pyrazole;
5-(4-chlorophenyl)-3-[1-(1-naphthylmethyl)piperidin-4-yl] pyrazole;
3-[1-(2-furylmethyl)piperidin-4-yl]-4-methyl-5-phenylpyrazole;
3-[1-(2-(4-methoxyphenyl)ethyl)piperidin-4-yl]-4-methyl-5-phenylpyrazole;
4-methyl-3-[1-(2-oxo-2-phenylethyl)piperidin-4-yl]-5-phenylpyrazole;
4-methyl-5-phenyl-3-[1-(2-(3-pyridyl)ethyl)piperidin-4-yl] pyrazole;
5-(4-chlorophenyl)-3-[1-(1,2,3,4-tetrahydronaphth-2-yl) piperidin-4-yl]pyrazole;
4-chloro-5-(4-chlorophenyl)-3-[1-(2-phenylethyl)piperidin-4-yl]pyrazole;
or a pharmaceutically acceptable salt or a prodrug thereof.

6. A pharmaceutical composition comprising a compound as claimed in claim 1 in association with a pharmaceutically acceptable carrier.

7. A process for the preparation of a compound as claimed in claim 1 which comprises:

(A) reacting a compound of formula II with a compound of formula III:

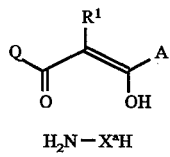
(II)

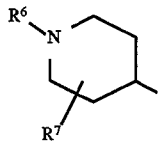
(III)

wherein Q, $R^1$ and A are as defined in claim 1, and $X^a$ represents oxygen, sulphur or N—$R^2$ in which $R^2$ is as defined in claim 1; followed, if necessary, by separation of the resulting mixture of isomers; or (B) for the preparation of a compound of formula I wherein X represents nitrogen, Y is N—$R^2$, $R^1$ is hydrogen and Q represents a group of formula Qa:

(Qa)

wherein $R^6$ are as defined in claim 1: reacting a compound of formula VIII:

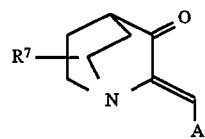
(VIII)

wherein A and $R^7$ are as defined in claim 1; with hydrazine hydrate; followed by attachment of the groups $R^6$ and $R^2$, where the latter is required to be other than hydrogen; and (C) subsequently, where required, converting a compound of formula I initially obtained into a further compound of formula I by conventional methods.

8. A method for the treatment and/or prevention of disorders of the dopamine system, which method comprises administering to a patient in need of such treatment an effective amount of a compound as claimed in claim 1.

9. A method for treating schizophrenia which comprises administering to a patient in need of such treatment a therapeutically effective amount of a compound as claimed in claim 1.

* * * * *

UNITED STATES PATENT AND TRADEMARK OFFICE
CERTIFICATE OF CORRECTION

PATENT NO. : 5,631,269
DATED : May 20, 1997
INVENTOR(S) : Broughton, et al

It is certified that error appears in the above-identified patent and that said Letters Patent is hereby corrected as shown below:

In column 2, line 41, "-$S_2NR^aR^b$" should be corrected to "-$SO_2NR^aR^b$".

In column 2, line 42, "-$C_2R^a$" should be corrected to "-$CO_2R^a$".

In column 3, line 47, heterocycloalkyl" should be so spelt.

In column 6, line 17, "cyclohexylmethyl" should be so spelt.

In column 9, lines 63-64, "insufflation" should be so spelt.

In column 13, line 10, "[3H]" should correctly read "[$^3$H]".

In column 31, line 26, "Qe" should read "Qc".

In column 32, line 30, "salt prodrug" should correctly read "salt or a prodrug".

UNITED STATES PATENT AND TRADEMARK OFFICE
CERTIFICATE OF CORRECTION

PATENT NO.   : 5,631,269
DATED        : May 20, 1997
INVENTOR(S)  : Broughton, et al It is certified that error appears in the above-identified patent and that said Letters Patent is hereby corrected as shown below:

In Claim 3, column 32, line 64 add the following:
"wherein
$Y^1$ represents oxygen, sulphur or $N-R^{12}$;
one of T and U represents CH and the other represents CH or N;
$R^{11}$ represents hydrogen, halogen, $C_{1-6}$alkyl or $C_{1-6}$alkoxy;
$R^{12}$ represents hydrogen or $C_{1-6}$alkyl;
$R^{13}$ represents hydrogen, halogen, trifluoromethyl, cyano, nitro, amino, $C_{1-6}$alkylamino, di($C_{1-6}$)alkylamino, $C_{1-6}$alkyl, $C_{1-6}$alkoxy, aryl ($C_{1-6}$)alkoxy or $C_{2-6}$alkylcarbonyl; $R^{16}$ represents $C_{2-6}$alkenyl, $C_{3-7}$cycloalkyl($C_{1-6}$)alkyl, aryl, aryl($C_{1-6}$)alkyl, aryl($C_{2-6}$)alkenyl or heteroaryl ($C_{1-6}$)alkyl, any of which groups may be optionally substituted; and $R^{17}$ represents hydrogen or methyl."

In Column 33, line 14, "cycano" should read "cyano".

In Column 35, line 23, after "$R^6$" the term "and $R^7$" should be added.

Signed and Sealed this

Seventeenth Day of March, 1998

Attest:

BRUCE LEHMAN

Attesting Officer

Commissioner of Patents and Trademarks